(12) United States Patent
Krupnik et al.

(10) Patent No.: US 10,101,890 B2
(45) Date of Patent: Oct. 16, 2018

(54) SYSTEM AND METHOD FOR DISPLAYING PORTIONS OF IN-VIVO IMAGES

(71) Applicant: GIVEN IMAGING LTD., Yoqneam (IL)

(72) Inventors: Hagai Krupnik, Nofit (IL); Eli Horn, Kiryat Motzkin (IL); Ady Ecker, Nes-Ziona (IL)

(73) Assignee: GIVEN IMAGING LTD., Yoqneam (IL)

( * ) Notice: Subject to any disclaimer, the term of this patent is extended or adjusted under 35 U.S.C. 154(b) by 284 days.

(21) Appl. No.: 14/713,016

(22) Filed: May 15, 2015

(65) Prior Publication Data

US 2015/0248223 A1 Sep. 3, 2015

Related U.S. Application Data

(63) Continuation of application No. 13/643,483, filed as application No. PCT/IL2011/000345 on Apr. 28, 2011, now Pat. No. 9,060,673.

(Continued)

(51) Int. Cl.
*G06K 9/00* (2006.01)
*G06F 3/0484* (2013.01)
(Continued)

(52) U.S. Cl.
CPC ...... *G06F 3/04845* (2013.01); *A61B 1/00009* (2013.01); *A61B 1/00045* (2013.01);
(Continued)

(58) Field of Classification Search
CPC ............ G06F 17/30256; G06F 3/0482; G06F 3/04842; G06F 3/04845; G06T 11/60;
(Continued)

(56) References Cited

U.S. PATENT DOCUMENTS

| 4,017,261 A | 4/1977 | Svoboda et al. |
| 4,243,652 A | 1/1981 | Francis |

(Continued)

FOREIGN PATENT DOCUMENTS

| CN | 101669807 | 3/2010 |
| DE | 344 0177 | 5/1986 |

(Continued)

OTHER PUBLICATIONS

U.S. Appl. No. 60/533,263, filed Dec. 31, 2003, Meron et al.

(Continued)

*Primary Examiner* — Nirav G Patel
(74) *Attorney, Agent, or Firm* — Pearl Cohen Zedek Latzer Baratz LLP

(57) ABSTRACT

A method and a system for displaying portions of in vivo images such as pathological or anatomical landmark portions of images, may include receiving a stream of in vivo images captured in a body lumen, and selecting relevant image portions such as suspected pathological image portions from the stream, based on one or more predetermined criteria. A spatial arrangement of the image portions may be determined, and the selected image portions may be resized to an appropriate size, and displayed in a rectangular or hexagonal array layout according to the determined spatial arrangement, such that rows and columns of selected image portions are adjacent to each other.

18 Claims, 11 Drawing Sheets

Related U.S. Application Data

(60) Provisional application No. 61/328,705, filed on Apr. 28, 2010.

(51) Int. Cl.

| | | |
|---|---|---|
| *G06T 3/40* | (2006.01) | |
| *A61B 1/00* | (2006.01) | |
| *A61B 1/04* | (2006.01) | |
| *A61B 1/045* | (2006.01) | |
| *G06T 11/60* | (2006.01) | |
| *G06F 3/0482* | (2013.01) | |
| *G06F 17/30* | (2006.01) | |
| *G06T 7/00* | (2017.01) | |

(52) U.S. Cl.
CPC .............. *A61B 1/041* (2013.01); *A61B 1/045* (2013.01); *G06F 3/0482* (2013.01); *G06F 3/04842* (2013.01); *G06F 17/30256* (2013.01); *G06T 3/4038* (2013.01); *G06T 7/0012* (2013.01); *G06T 11/60* (2013.01)

(58) Field of Classification Search
CPC . G06T 3/4038; G06T 7/0012; A61B 1/00009; A61B 1/00045; A61B 1/041; A61B 1/045
See application file for complete search history.

(56) References Cited

U.S. PATENT DOCUMENTS

| | | |
|---|---|---|
| 4,278,077 A | 7/1981 | Mizumoto |
| 4,337,222 A | 6/1982 | Kitajima et al. |
| 4,698,664 A | 10/1987 | Nichols et al. |
| 4,907,095 A | 3/1990 | Komura et al. |
| 4,920,045 A | 4/1990 | Okuda et al. |
| 4,938,823 A | 7/1990 | Balazek et al. |
| 5,381,784 A | 1/1995 | Adair |
| 5,494,032 A | 2/1996 | Robinson |
| 5,566,169 A | 10/1996 | Rangan et al. |
| 5,603,687 A | 2/1997 | Hori et al. |
| 5,604,531 A | 2/1997 | Iddan et al. |
| 5,605,153 A | 2/1997 | Fujioka et al. |
| 5,642,157 A | 6/1997 | Shibanuma et al. |
| 5,697,384 A | 12/1997 | Miyawaki et al. |
| 5,697,885 A | 12/1997 | Konomura et al. |
| 5,726,670 A | 3/1998 | Tabata et al. |
| 5,880,777 A | 3/1999 | Savoye et al. |
| 5,993,378 A | 11/1999 | Lamelson |
| 6,173,317 B1 | 1/2001 | Chaddha |
| 6,208,354 B1 | 3/2001 | Porter |
| 6,240,312 B1 | 5/2001 | Alfano et al. |
| 6,289,165 B1 | 9/2001 | Abecassis |
| 6,339,446 B1 | 1/2002 | Miyoshi |
| 6,504,990 B1 | 1/2003 | Abecassis |
| 6,563,959 B1 | 5/2003 | Troyanker |
| 6,654,539 B1 | 11/2003 | Duruoz et al. |
| 6,709,387 B1 | 3/2004 | Glukhovsky et al. |
| 6,741,977 B1 | 5/2004 | Nagaya et al. |
| 6,764,440 B2 | 7/2004 | Iddan et al. |
| 6,791,601 B1 | 9/2004 | Chang et al. |
| 6,902,581 B2 | 6/2005 | Walkenhorst et al. |
| 6,904,308 B2 | 6/2005 | Frisch et al. |
| 6,944,316 B2 | 9/2005 | Glukhovsky et al. |
| 6,950,690 B1 | 9/2005 | Meron et al. |
| 6,976,229 B1 | 12/2005 | Balabanovic et al. |
| 7,009,634 B2 | 3/2006 | Iddan et al. |
| 7,027,633 B2 | 4/2006 | Foran et al. |
| 7,119,814 B2 | 10/2006 | Meron et al. |
| 7,200,253 B2 | 4/2007 | Glukhovsky et al. |
| 7,260,777 B2 | 8/2007 | Fitzsimons et al. |
| 7,272,657 B2 | 9/2007 | Allen et al. |
| 7,324,673 B1 | 1/2008 | Yamanaka et al. |
| 7,392,233 B2 | 6/2008 | Tanaka |
| 7,452,328 B2 | 11/2008 | Homan et al. |
| 7,474,327 B2 | 1/2009 | Davidson |
| 7,505,062 B2 | 3/2009 | Davidson et al. |
| 7,577,283 B2 | 8/2009 | Zinaty et al. |
| 7,986,337 B2 | 7/2011 | Davidson et al. |
| 8,045,000 B2 | 10/2011 | Davidson et al. |
| 8,164,672 B2 | 4/2012 | Meron et al. |
| 8,682,142 B1 | 3/2014 | Boskovitz et al. |
| 2001/0015753 A1 | 8/2001 | Myers |
| 2001/0031920 A1 | 10/2001 | Kaufman et al. |
| 2001/0035902 A1 | 11/2001 | Iddan et al. |
| 2002/0021828 A1 | 2/2002 | Papier et al. |
| 2002/0103417 A1 | 8/2002 | Gazdzinski |
| 2002/0109774 A1 | 8/2002 | Meron et al. |
| 2002/0140861 A1 | 10/2002 | Janevski et al. |
| 2002/0149693 A1 | 10/2002 | Tantalo et al. |
| 2002/0177779 A1 | 11/2002 | Adler et al. |
| 2003/0086596 A1 | 5/2003 | Hipp et al. |
| 2003/0151661 A1 | 8/2003 | Davidson et al. |
| 2003/0167000 A1 | 9/2003 | Mullick et al. |
| 2003/0174208 A1 | 9/2003 | Glukhovsky et al. |
| 2003/0208107 A1 | 11/2003 | Refael |
| 2004/0027500 A1 | 2/2004 | Davidson et al. |
| 2004/0249291 A1 | 12/2004 | Honda et al. |
| 2004/0268389 A1 | 12/2004 | Sezan et al. |
| 2005/0038321 A1 | 2/2005 | Fujita et al. |
| 2005/0074151 A1 | 4/2005 | Chen et al. |
| 2005/0075537 A1 | 4/2005 | Chen et al. |
| 2005/0075551 A1 | 4/2005 | Horn et al. |
| 2005/0110948 A1 | 5/2005 | Bille et al. |
| 2006/0036131 A1 | 2/2006 | Glukhovsky et al. |
| 2006/0053150 A1 | 3/2006 | Taguchi et al. |
| 2006/0074275 A1 | 4/2006 | Davidson et al. |
| 2006/0079761 A1* | 4/2006 | Tu .......................... G06K 9/4614 600/425 |
| 2006/0106318 A1 | 5/2006 | Davidson |
| 2006/0164511 A1 | 7/2006 | Krupnik |
| 2006/0187300 A1 | 8/2006 | Davidson et al. |
| 2007/0078335 A1 | 4/2007 | Horn |
| 2007/0211802 A1 | 9/2007 | Kikuchi et al. |
| 2007/0230893 A1 | 10/2007 | Meron et al. |
| 2008/0039692 A1 | 2/2008 | Hlrakawa |
| 2008/0075172 A1 | 3/2008 | Koto et al. |
| 2009/0016491 A1 | 1/2009 | Li |
| 2009/0074265 A1 | 3/2009 | Huang et al. |
| 2009/0135250 A1 | 5/2009 | Davidson |
| 2009/0148058 A1 | 6/2009 | Dane et al. |
| 2009/0201985 A1 | 8/2009 | Ramanzin |
| 2009/0228834 A1 | 9/2009 | Reynolds |
| 2009/0309961 A1 | 12/2009 | Miyashita |
| 2010/0014738 A1* | 1/2010 | Birnholz .................. G06T 7/0012 382/131 |
| 2010/0108769 A1 | 5/2010 | Wang et al. |
| 2011/0085022 A1 | 4/2011 | Wang |
| 2011/0164126 A1 | 7/2011 | Ambor et al. |
| 2011/0243523 A1 | 10/2011 | Davidson et al. |
| 2012/0038762 A1 | 2/2012 | Davidson et al. |
| 2012/0069049 A1 | 3/2012 | Howe et al. |
| 2012/0113239 A1 | 5/2012 | Krupnik et al. |

FOREIGN PATENT DOCUMENTS

| | | |
|---|---|---|
| EP | 1790277 | 5/2007 |
| JP | 57-45833 | 3/1982 |
| JP | 61-143876 | 7/1986 |
| JP | 63-214231 | 9/1988 |
| JP | 63214231 | 9/1988 |
| JP | 02-286124 | 11/1990 |
| JP | 04109927 | 4/1992 |
| JP | 4-144533 | 5/1992 |
| JP | 1992-144533 | 5/1992 |
| JP | 10112835 | 4/1998 |
| JP | 2000-047651 | 2/2000 |
| JP | 2001-167248 | 6/2001 |
| JP | 2002/503046 | 1/2002 |
| JP | 2003-038424 | 2/2003 |
| JP | 2004521662 | 7/2004 |
| JP | 2004321603 | 11/2004 |
| JP | 2006280792 | 10/2006 |
| JP | 2007519440 | 7/2007 |
| JP | 2009226170 | 10/2009 |

(56) References Cited

FOREIGN PATENT DOCUMENTS

| WO | WO 99/40587 | 8/1999 |
|----|----|----|
| WO | WO 2000/022975 | 4/2000 |
| WO | WO 01/50180 | 7/2001 |
| WO | WO 01/50941 | 7/2001 |
| WO | WO 01/65995 | 9/2001 |
| WO | WO 02/054932 | 7/2002 |
| WO | WO 2002/073507 | 9/2002 |
| WO | WO 2003/069913 | 8/2003 |
| WO | WO 2005/062715 | 7/2005 |
| WO | WO 2009/008125 | 1/2009 |
| WO | WO 2011/135573 | 11/2011 |

OTHER PUBLICATIONS

U.S. Appl. No. 13/051,299, filed Mar. 18, 2011, Boskovitz et al.
U.S. Appl. No. 13/051,229, filed Mar. 18, 2011, Boskovitz et al.
Sample Picasa screenshot printed Dec. 2011.
www.zdnet.co.uk/pcmag/trends/2001/04/06.html, "Perfect motion on the Net"—Cliff Joseph, printed Dec. 25, 2001.
www.dynapel.com, Motion Perfect® Product Literature, printed Jul. 22, 2003.
Jun Yang et al., "Two Image Photometric Stereo Method", Department of Information Engineering, Nagoya University, SPIE vol. 1826 Intelligent Robots and Computer Vision XI (1992) pp. 452-463.
synQUAD Technology Synchronized nQUAD Technology printed Mar. 15, 2000.
Puzicha, J. "Empirical Evaluation of Dissimilarity Measures for Color and Texture," Computer Vision and Image Understanding, 84, 2001, pp. 25-43.
Lehmann, T., "Content-Based Image Retrieval in Medical Applications: A Novel-Step Approach", Proc. SPIE 2000, vol. 3972, pp. 312-320.
Roubik et al., "Reference Microelectrodes Design Evaluation for On-Chip ISFET-Based Microsensors for 'in vivo' Blood Measurements".
www.obsltd.co.uk—Data warehousing—Jan. 22, 2001.
In vivo luecocyte adhesion to modified polyurethane surfaces—Bruil pp. 915-923. Biomaterials 1992.vol. 13 No. 13.
International Search Report and written opinion issued for PCT/IL11/00345, dated Sep. 22, 2011.
Office Action for U.S. Appl. No. 10/584,997 dated Mar. 30, 2009.
Office Action for U.S. Appl. No. 10/584,997 dated Feb. 17, 2011.
Office Action for U.S. Appl. No. 12/323,620 dated Feb. 4, 2011.
Office Action for U.S. Appl. No. 10/610,915 dated Feb. 7, 2008.
Office Action for U.S. Appl. No. 10/610,915 dated Oct. 27, 2006.
Office Action for U.S. Appl. No. 10/986,918 dated Sep. 22, 2005.
Final Office Action for U.S. Appl. No. 10/986,918 dated Apr. 6, 2006.
Final Office Action for U.S. Appl. No. 10/364,508 dated Jan. 23, 2007.
Office Action for U.S. Appl. No. 10/364,508 dated Jun. 7, 2006.
Office Action for U.S. Appl. No. 10/364,508 dated Jun. 5, 2007.
Final Office Action for U.S. Appl. No. 10/610,915 dated May 17, 2007.
Office Action for U.S. Appl. No. 10/364,508 dated Jan. 23, 2008.
Final Office Action for U.S. Appl. No. 10/584,997 dated Sep. 14, 2009.
Office Action for U.S. Appl. No. 11/321,456 dated Jun. 25, 2010.
Office Action for U.S. Appl. No. 11/321,456 dated Dec. 3, 2010.
Final Office Action for U.S. Appl. No. 10/584,997 dated Jul. 9, 2010.
Office Action for U.S. Appl. No. 10/584,997 dated Jan. 14, 2010.
Office Action for U.S. Appl. No. 10/584,997 dated Aug. 31, 2011.
Final Office Action for U.S. Appl. No. 11/358,401 dated Aug. 5, 2011.
Office Action for U.S. Appl. No. 11/358,401 dated Apr. 24, 2009.
Office Action for U.S. Appl. No. 11/358,401 dated Oct. 22, 2008.
Final Office Action for U.S. Appl. No. 11/358,401 dated Aug. 24, 2010.
Final Office Action for U.S. Appl. No. 11/358,401 dated Nov. 25, 2009.
Office Action for U.S. Appl. No. 11/358,401 dated Mar. 17, 2010.
Final Office Action for U.S. Appl. No. 11/358,401 dated Feb. 10, 2011.
Analysis and Decision Support Methods for Capsule Endoscopy, Methods Designed to Enhance the Capsule Endoscopy Study Diagnosis Process, John Hopkins Technology Transfer, Whiting School of Engineering, as of Feb. 2010.
Office Action for U.S. Appl. No. 13/051,229 dated Nov. 9, 2012.
Final Office Action for U.S. Appl. No. 13/051,229 dated Apr. 2, 2013.
Notice of Allowance for U.S. Appl. No. 13/051,229 dated Nov. 4, 2013.
Office Action for U.S. Appl. No. 13/291,245 dated Nov. 7, 2013.
Notice of Allowance for U.S. Appl. No. 10/610,915 dated Sep. 11, 2007.
Office Action for U.S. Appl. No. 13/161,845 dated Jun. 20, 2013.
Notice of Allowance for U.S. Appl. No. 13/161,845 dated Jan. 21, 2014.
Office Action for U.S. Appl. No. 10/949,220 dated Mar. 17, 2008.
Final Office Action for U.S. Appl. No. 10/949,220 dated Aug. 27, 2008.
Office Action for U.S. Appl. No. 10/949,220 dated Feb. 20, 2009.
Final Office Action for U.S. Appl. No. 10/949,220 dated Jul. 29, 2009.
Office Action for U.S. Appl. No. 10/949,220 dated Dec. 24, 2009.
Final Office Action for U.S. Appl. No. 10/949,220 dated Jul. 2, 2010.
Office Action for U.S. Appl. No. 10/949,220 dated Sep. 10, 2010.
Notice of Allowance for U.S. Appl. No. 10/949,220 dated Mar. 17, 2011.
Advisory Action for U.S. Appl. No. 10/949,220 dated Aug. 31, 2010.
Advisory Action for U.S. Appl. No. 13/051,229 dated Jun. 18, 2013.
Advisory Action for U.S. Appl. No. 13/051,229 dated Aug. 1, 2013.
Office Action for U.S. Appl. No. 13/643,483 dated May 20, 2014.
Final Office Action of U.S. Appl. No. 13/291,245 dated Apr. 10, 2014.
Office Action of U.S. Appl. No. 13/279,515 dated Aug. 13, 2014.
Notice of Allowance of U.S. Appl. No. 13/279,515 dated Nov. 7, 2014.
Final Office Action of U.S. Appl. No. 13/643,483 dated Sep. 10, 2014.
Advisory Action of U.S. Appl. No. 13/643,483 dated Nov. 17, 2014.
Notice of Allowance of U.S. Appl. No. 13/643,483 dated Feb. 18, 2015.
U.S. Appl. No. 10/986,918, filed Nov. 15, 2004, Davidson.

\* cited by examiner

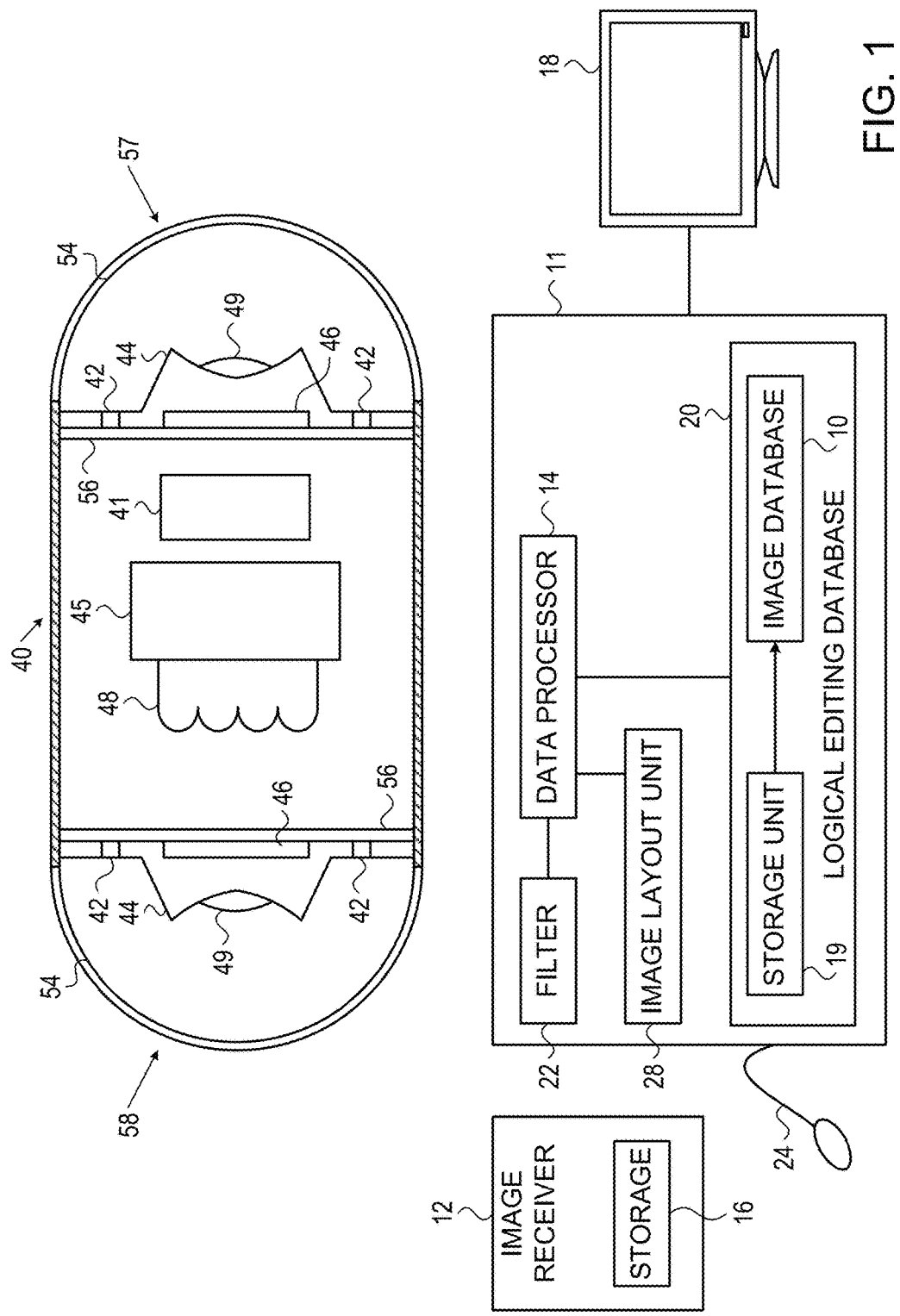

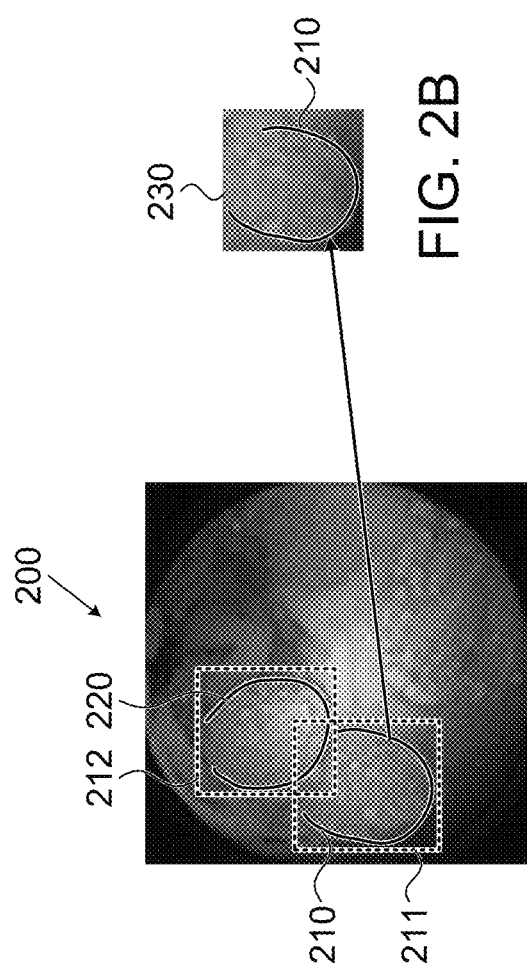

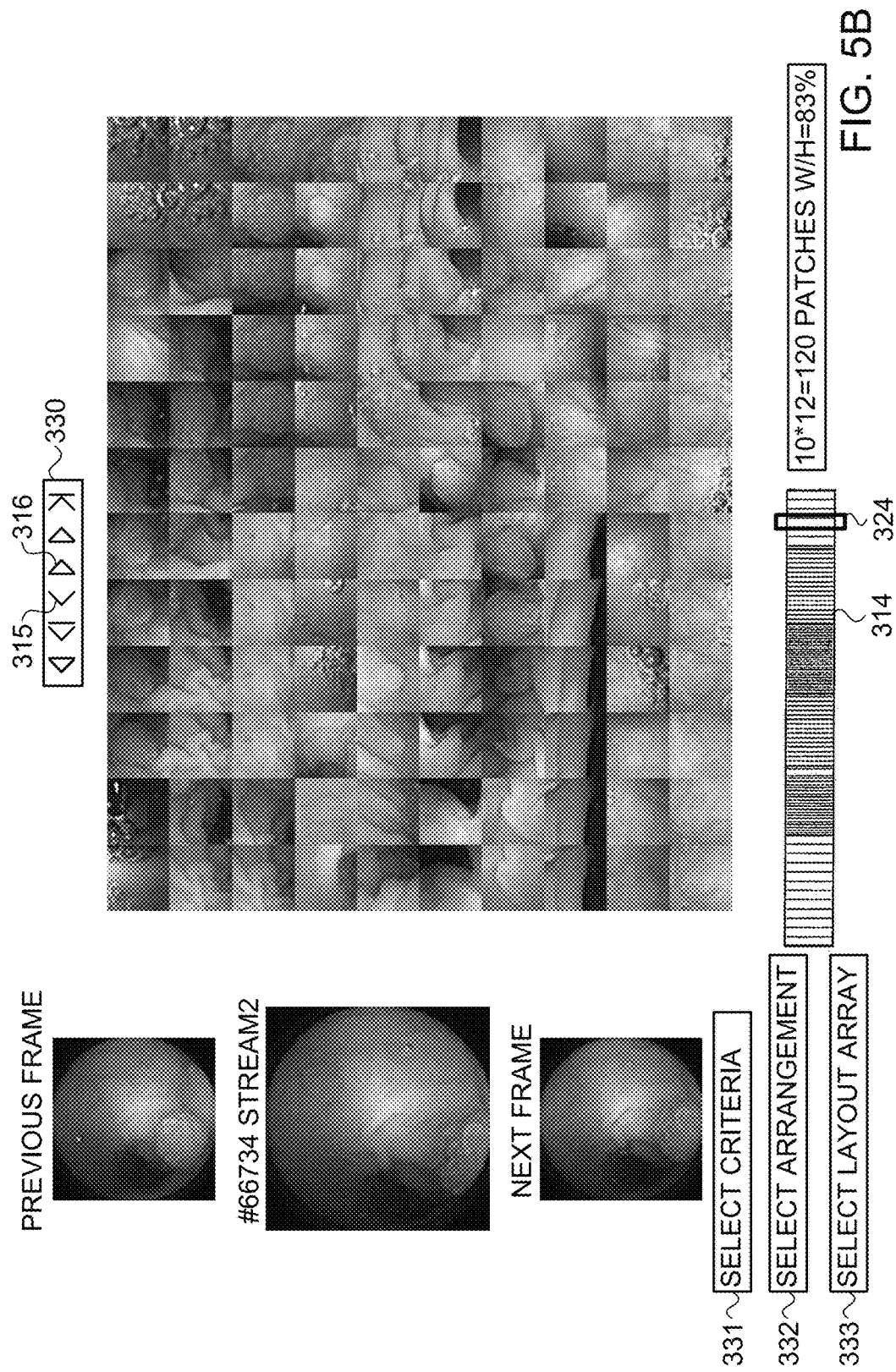

SYSTEM AND METHOD FOR DISPLAYING PORTIONS OF IN-VIVO IMAGES

CROSS-REFERENCE TO RELATED APPLICATIONS

This application is a continuation of U.S. patent application Ser. No. 13/643,483 filed Jan. 4, 2013, which is a National Phase Application of PCT International Application No. PCT/IL2011/000345 filed Apr. 28, 2011, which in turn claims priority from U.S. patent application Ser. No. 61/328,705 filed Apr. 28, 2010, all of which are incorporated herein by reference in their entirety.

FIELD OF THE INVENTION

The present invention relates to a method and system for displaying an image stream captured in-vivo. More specifically, the present invention relates to systems and methods for arranging and displaying image portions, for example in the form of an array.

BACKGROUND OF THE INVENTION

In-vivo imaging methods, such as an in-vivo imaging system which is carried by an ingestible capsule, may be used to image body lumens within a patient. The imaging system may capture and transmit, for example, images of the gastrointestinal (GI) tract to an external recording device, while the capsule passes through the GI lumen. Such an in-vivo imaging system provides a platform from which moving image streams or still images of a body lumen may be viewed. Large numbers of images, for example 100,000 to 300,000 images, may be collected for viewing during the imaging procedure. The images may be combined in sequence, and an image stream or movie of, for example, 30-120 minutes in length, may be presented to a user.

A user, e.g. a physician or health care professional, may view a complete image stream, e.g., the original stream of images captured by the in-vivo device, or a slightly reduced stream of images (e.g. in which similar images are merged or removed), and substantially all images which differ from each other are presented. When viewing such streams, the user may typically use a relatively fast display rate of, for example, 20-30 frames per second.

A user may want to reduce viewing time of the image stream. Known methods for reducing a viewing time exist. For example, a summary movie of the entire image stream may be generated, based on editing methods. Editing methods may include, for example, selecting images which follow predetermined criteria. A shortened movie may be created, assisting the physician to reduce viewing time.

However, viewing a summary movie may have certain drawbacks or disadvantages. For example, substantially identical images may contain pathologies. Redundant images may be filtered from the summary movie, and in some cases only one or a few representative image frames which contain the pathology may be presented in the summary movie.

It would be desirable to provide a user, for example a physician, a different view or display of images, which on one hand allows for a closer inspection of images or portions of images, and on the other hand does not increase the viewing time, at least not significantly.

SUMMARY OF THE INVENTION

In one embodiment, a method and system are provided for displaying portions of in vivo images. The method may include receiving a stream of in vivo images captured in a body lumen. Image portions or images depicting or corresponding to a suspected pathology may be selected from the stream, for example based on one or more selection criteria. The image portions may be cropped, resized to an appropriate size, and may be spatially arranged according to a selected distribution or layout arrangement, for example in a rectangular or hexagonal array layout. Rows and columns of the selected image portions may be positioned adjacent to each other, for example with no white space, border or background between the adjacent image portions. E.g., image pixels of one image may be touching or directly adjacent to image pixels of another image, without an intermediate non-image pixels.

In some embodiments, the number of image portions to be displayed in the rectangular array layout may be predetermined, set by a user, or adjusted based on the number of suspected pathological image portions that are found in the image stream. A spatial arrangement of the image portions in the layout may be determined or selected, and a time bar with a cursor indicating the capture time of the image portions displayed in the current layout may be displayed.

Some embodiments include determining a similarity between the selected image portions which are to be displayed. The similar image portions may be arranged in a chronological sequence in the layout. In another embodiment, all the suspected pathological image portions may be arranged in chronological sequence in the layout. In one embodiment, the complete image frame corresponding to an image portion marked by a user in the layout may be displayed.

The selection criteria may be determined, for example by a user or predetermined and stored in the system.

BRIEF DESCRIPTION OF THE DRAWINGS

The principles and operation of the system and method according to the present invention may be better understood with reference to the drawings, and the following description, it being understood that these drawings are given for illustrative purposes only and are not meant to be limiting, wherein:

FIG. 1 shows a schematic diagram of an in-vivo imaging system according to an embodiment of the present invention;

FIGS. 2A and 2B illustrate an image with a suspected pathology according to an embodiment of the present invention;

FIGS. 5A and 5B are exemplary spatial arrays displaying different sizes of layouts, according to an embodiment of the present invention;

Figure 3A:
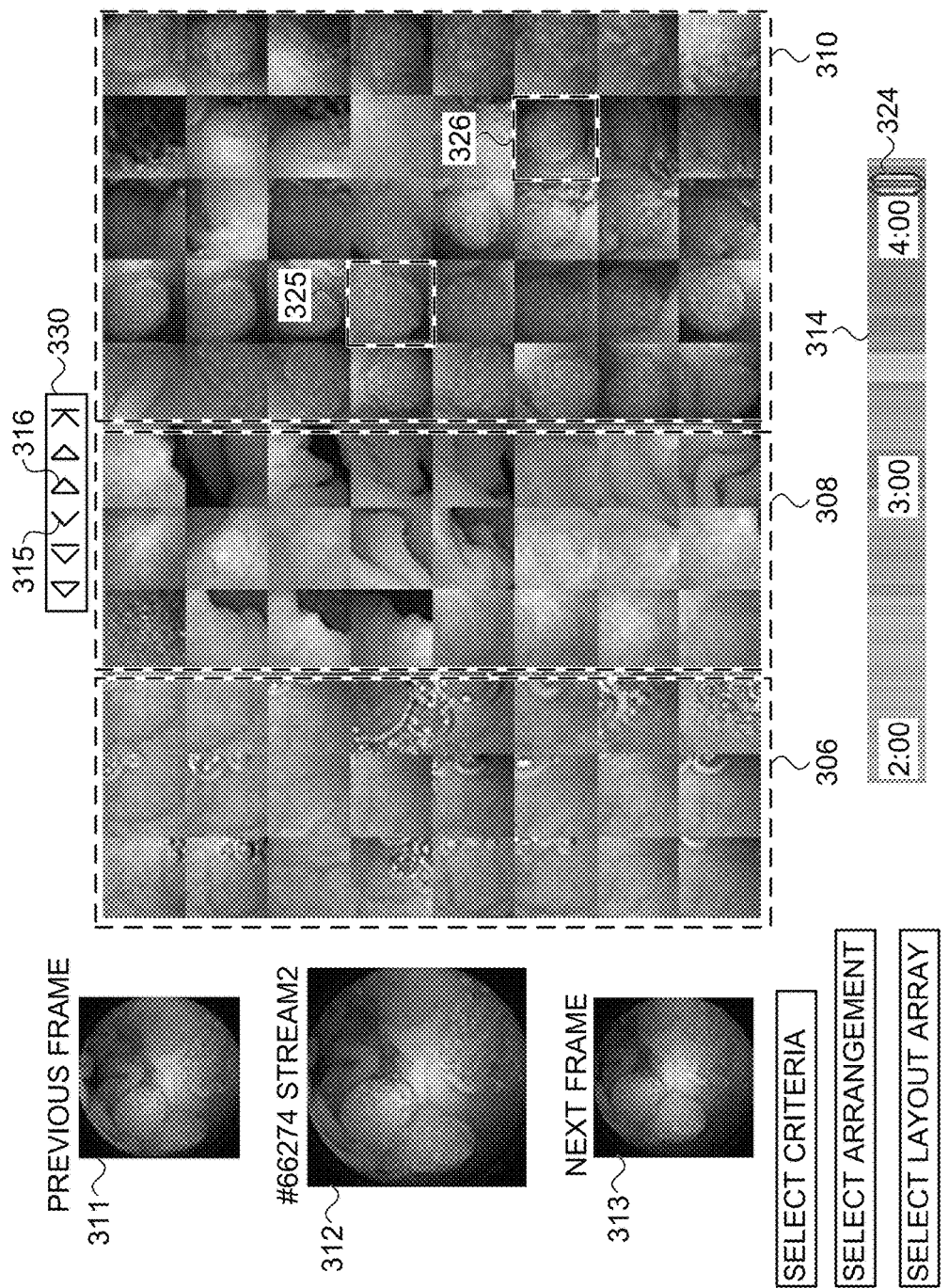
FIGS. 3A and 3B are exemplary display interfaces, showing an example of one set (array) of pathological frame portions compared to another set of frame portions containing normal healthy tissue according to an embodiment of the present invention.

It will be appreciated that for simplicity and clarity of illustration, elements shown in the figures have not necessarily been drawn to scale. For example, the dimensions and/or aspect ratio of some of the elements may be exaggerated relative to other elements for clarity. Further, where considered appropriate, reference numerals may be repeated among the figures to indicate corresponding or analogous elements throughout the serial views.

DETAILED DESCRIPTION OF THE INVENTION

In the following description, various aspects of the present invention will be described. For purposes of explanation, specific configurations and details are set forth in order to provide a thorough understanding of the present invention. However, it will also be apparent to one skilled in the art that the present invention may be practiced without the specific details presented herein. Furthermore, well known features may be omitted or simplified in order not to obscure the present invention.

Unless specifically stated otherwise, as apparent from the following discussions, it is appreciated that throughout the specification discussions utilizing terms such as "processing", "computing", "storing", "determining", or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

Some embodiments of the present invention are directed to a swallowable in-vivo device, such as an autonomous swallowable capsule. Other embodiments need not be swallowable or autonomous, and may have other shapes or configurations. Devices according to embodiments of the present invention, including imaging, receiving, processing, storage and/or display units suitable for use with embodiments of the present invention, may be similar to embodiments described in US Patent Application Publication Number 2006/0074275, entitled "SYSTEM AND METHOD FOR EDITING AN IMAGE STREAM CAPTURED IN-VIVO", U.S. Pat. No. 5,604,531 to Iddan et al., entitled "In-vivo Video Camera System", and/or in U.S. Pat. No. 7,009,634 to Iddan et al., entitled "Device for In-Vivo Imaging", all of which are hereby incorporated by reference in their entirety. Of course, devices and systems as described herein may have other configurations and other sets of components. Devices, systems and methods according to some embodiments of the present invention, may be similar to the commercial PillCam® SB2 or PillCam® Colon capsules and the associated data recorders and RAPID® workstation and software provided by Given Imaging, Ltd.

In one embodiment, a user, for example a physician, may view a layout of images or image portions, arranged for example in tiled or grid array. The layout may contain a subset of images from an input image stream captured during an imaging procedure, or selected portions of the subset of images. The array or grid may be, for example, a square or rectangular or hexagonal array, and the selected portions or images may be arranged to improve the efficiency of the review by a user. The images or portions thereof, may be selected based on one or more predetermined criteria. Typically, the images are selected based on criteria that indicate possible pathology in the images. In another example, the images may be selected based on criteria that indicates possible landmarks in the imaged body lumen, such as entrance to the small bowel, entrance to the colon, etc. The array may include a predetermined or a varying amount of images or portions thereof, and a plurality of arrays may be generated and displayed to the user, for example in accordance with the total number of images which were selected from the original input image stream.

An abnormality of the tissue may be prominent or may catch the eye of a user looking at multiple images or portions thereof which contain normal tissue as well as pathology. Similarly, if only normal tissue is presented in the array of images or image portions, the user may quickly determine that no pathology is present in the current layout of images, and may scroll (e.g., use an input device to cause the display to redisplay or move) to the next array for its inspection. The user may scroll through one or more arrays of images or image portions, which may be spatially arranged on the display device in order to allow easier or quicker detection of abnormal tissue or tissue suspected as being pathological. In contrast with a video display wherein each frame is displayed during a relatively short, pre-determined time slot and replaced automatically by a consecutive image, this review method may allow each suspected portion a relatively longer display time and the user may have to actively scroll to the next array. Additionally, in a video or image stream display, the viewer is exposed to entire frames such that the user is required to analyze the content of suspected and non-suspected portions alike, whereas a review method based on arrays of suspected portions and images, may remove non-suspected image portions to save time required for a full frame analysis. Such a review method may save the viewing physician time, while enabling a reliable diagnosis with increased probability of finding a pathological, suspicious or abnormal image.

An exemplary embodiment of the present invention provides a system and method for displaying an image stream, the image stream preferably being produced by an in-vivo imaging device such as an ingestible or swallowable capsule. A workstation may accept the in vivo images and may display a subset of the images or selected portions of a subset of the image frames, for example as a plurality of layouts such as rectangular tiled arrays or grids on a display device or monitor.

The image stream may be edited and reduced, or a subset of images to be viewed may be selected for initial viewing or preview, using editing methods which may include any number of methods based on pre-determined frame selection and frame skipping, or methods based on algorithmic recognition of pre-determined criteria, e.g. images pertaining to a known symptom, such as polyps, bleeding and/or ulcers, etc. Editing methods used by embodiments of the invention may be similar to and/or may include methods described in US Patent Publication Number 2006/0074275, titled "System and Method for Editing an Image Stream Captured In Vivo" and/or US Patent Publication Number 2007/0078335, titled "System and Method for In Vivo Feature Detection." For example, an embodiment corresponding to FIG. 2 of US Patent Publication Number 2007/0078335, teaches the identification of a portion of an image suspected of depicting pathological tissue, such as a polyp.

One or more arrays or grids of images or portions of images may be generated and displayed in a specific spatial layout according to embodiments of the present invention. In some embodiments, the images or portions thereof may include selected images for display, for example images or portions of images corresponding to one or more predetermined criteria. Preferably, the selection of images or portions thereof for display includes selected images detected or filtered automatically by a processor or filter, according to one or more predetermined criteria. Selected images or selected portions of images may include, for example: pathological images (or portions) such as portions of images detected by a polyp detector and indicated as possibly containing a polyp, portions of images detected by a blood detector as suspicious of containing blood, images detected by a lesion detector as potentially containing a lesion, and portions of images detected by an abnormality detector as possibly containing abnormal tissue instead of expected normal tissue. Such portions may include tissue having higher level of redness than surrounding tissue and/or shapes, patterns or texture typical for certain gastrointestinal disease or pathologies such as edema, erosion, erythema, inflammation, neoplasia, or polyps.

In one example, a selected portion of an image may contain, for example, substantially the portion of the image which contains the detected pathology or the suspected abnormality, or a frame or cropped version of the image where a greater portion of the frame or cropped version of the image contains the suspected abnormality or pathology than the original image. For example, a suspected polyp which was identified by a polyp detector may be included in a selected portion of an image. In addition to the suspected polyp, some surrounding background pixels which do not make up the suspected pathology may also be included in the selected portion of the image. This is primarily due to the need of a reviewer to see the suspected pathology in the context of the tissue area, and adding some background pixels, may allow the user to identify the suspected pathology better. In addition, the selected portion of the image is typically rectangular, square or hexagonal, but the suspected pathologies boundaries may be formed in a variety of different shapes. In another example, the selected portion of an image may contain the portion of a frame which was detected by a blood detector as depicting or corresponding to suspected bleeding. In yet another example, the selected portion of an image, may contain a suspected lesion, ulcer, inflammation, etc. The frame or cropped version may omit a portion of the image not containing the detected abnormality, but since the selected portion or cropped version is typically in a square, rectangular or hexagonal form, some sections or pixels of the selected portion may not include an abnormality, for example pixels which include tissue nearby the suspected pathology may be included in the cropped version of the image.

Reference is made to FIG. 1, which schematically illustrates an in-vivo imaging system according to an embodiment of the invention. According to some embodiments, the system may include a device, for example, a capsule 40. Capsule 40 may be a swallowable in-vivo capsule, but other sorts of devices or suitable implementations may be used. According to one embodiment, capsule 40 may communicate with an external receiving and display system to provide display of data, control, or other functions. For example, power may be provided by an internal battery 45 or a wireless receiving system. Other embodiments may have other configurations and capabilities.

Capsule 40 may include one or more imagers 46, for capturing images, one or more illumination sources 42, for illuminating the body lumen, and a transmitter 41, for transmitting image data and possibly other information to a receiving device such as receiver 12. Transmitter 41 may include receiver capability, for example, to receive control information. In some embodiments, the receiver capcbility may be included in a separate component. An optical system, including, for example, lenses 49, lensholders 44 or mirrors, may aid in focusing reflected light onto the imagers 46. The lenholders 44, illumination units 42, and imagers 46 may be mounted on a substrate 56. An imaging head 57 and/or 58 may include the optical system, optical dome 54, imager 46, illumination units 42, and substrate 56.

Preferably, located outside the patient's body in one or more locations, are an image receiver 12, preferably including an antenna or antenna array, an image receiver storage unit 16, a data processor 14, a data processor storage unit 19, and an image monitor 18, for displaying, for example, the images recorded by the capsule 40. Preferably, the image receiver 12 and image receiver storage unit 16 are small and portable, and are worn on the patient's body during recording of the images. The data processor 14, data processor storage unit 19, and image monitor 18 may be included in a computer or workstation 11.

According to embodiments of the present invention, data processor storage unit 19 may include an image database 10 and a logical editing database 20. Logical editing database 20 may include, for example, pre-defined criteria and rules for selecting images or portions thereof, stored in the image database 10, to be displayed to the viewer (e.g., in viewing window 200 of FIG. 2). In some embodiments, a list of the pre-defined criteria and rules may be displayed for selection by the viewer (e.g., associated with 'select criteria' button of FIGS. 3A and 3B). In other embodiments, rules or criteria need not be selectable by a user. Examples of selection criteria may include, but are not limited to: average intensity of the image, average value of the R, B, or G pixels in the image, median value of the pixel intensity, criteria based on HSV color space, B/R, G/R, STD (standard deviation) values of the previous criteria, differences between images, etc. In some embodiments, a plurality of certain criteria may be associated to a rule or detector, for example, a polyp detector may use several criteria to determine whether a candidate polyp is present in the image. Similarly, a bleeding or redness detector may use different criteria to determine whether the image includes suspected bleeding or pathological tissue having an abnormal level of redness. In some embodiments, the user may decide which rules and/or detectors to activate.

According to one embodiment of the invention, data processor 14, data processor storage unit 19 and monitor 18 are part of a personal computer or workstation 11 which includes standard components such as a processor, a memory, a disk drive, and input-output devices, although alternate configurations are possible, and the system and method of the present invention may be implemented on various suitable computing systems. An input device 24 may receive input from a user (e.g., via a pointing device, click-wheel or mouse, keys, touch screen, recorder/microphone, other input components) and send corresponding commands to trigger control of the computer components, e.g., data processor 14.

Data processor 14 may include one or more standard data processors, such as a microprocessor, multiprocessor, accelerator board, or any other serial or parallel high performance data processor. Image monitor 18 may be a computer screen, a conventional video display, or any other device capable of providing image or other data.

Preferably, the imager 46 is a suitable ccomplementary metal-oxide-semiconductor (CMOS) camera, such as a "camera on a chip" type CMOS imager specified by Given Imaging Ltd. of Israel and designed by Aptina Corporation of California, USA. In alternate embodiments, the imager 46 may be another device, for example, a charge-coupled device (CCD). The illumination source 42 may be, for example, one or more light emitting diodes, or another suitable light source.

During an in vivo imaging procedure, imager 46 may capture images and send data representing the images to transmitter 41, which transmits images to image receiver 12 using, for example, electromagnetic radio waves. Other signal transmission methods are possible and, alternatively, data may be dowloaded from capsule 40 after the procedure. Image receiver 12 may transfer the image data to image receiver storage unit 16. After a certain period of time of data collection, the image data stored in storage unit 16 may be sent to the data processor 14 or the data processor storage unit 19. For example, the image receiver storage unit 16 may be taken off the patient's body and connected to the personal computer or workstation which includes the data processor 14 and data processor storage unit 19 via a standard data link, e.g., a serial or parallel interface of known construction. The image data may then be transferred from the image receiver storage unit 16 to the image database 10 within data processor storage unit 19. In other embodiments, the data may be transferred from the image receiver storage unit 16 to the image database 10 using a wireless communiation protocol, such as Bluetooth, WLAN, or other wireless network protocols.

Data processor 14 may analyze and edit the data, for example, according to the logical editing database 20, and provide the analyzed and edited data to the image monitor 18, where for example a health professional views the image data. Data processor 14 may operate software which, in conjunction with basic operating software such as an operating system and device drivers, controls the operation of data processor 14. According to one embodiment, the software controlling data processor 14 may include code written, for example, in the C++ language and possibly alternative or additional languages, and may be implemented in a variety of known methods.

The image data collected and stored may be stored indefinitely, transferred to other locations, manipulated or analyzed. A health professional may use the images to diagnose pathological conditions of, for example, the GI tract, and in addition, the system may provide information about the location of these pathologies. While using a system where the data processor storage unit 19 first collects data and then transfers data to the data processor 14, the image data is not viewed in real time, other configurations allow for real time or quasi-real time viewing.

According to one embodiment, the capsule 40 may collect a series of still images as it traverses the GI tract. The images may be later presented as, for example, a stream of images or a moving image of the traverse of the GI tract. One or more in-vivo imager systems may collect a large volume of data, as the capsule 40 may take several hours to traverse the GI tract. The imagers 46 may record images at a rate of, for example, two to forty images per second (other rates, such as four frames per minute, may be used). The imagers 46 may have a fixed or variable frame capture and/or transmission rate. When the imagers 46 have a variable or adaptive frame rate (AFR), the imagers 46 may switch back and forth between frame rates, for example, based on parameters, such as the capsule 40 speed, its estimated location, similarity between consecutive images, or other criteria. A total of thousands of images, for example, over 300,000 images, may be recorded. The image recordation rate, the frame capture rate, the total number of images captured, the total number of images selected for the edited moving image, and the view time of the edited moving image, may each be fixed or varied.

Preferably, the image data recorded and transmitted by the capsule 40 is digital color image data, although in alternate embodiments other image formats may be used. In an exemplary embodiment, each frame of image data includes 256 rows of 256 pixels each, each pixel including bytes for color and brightness, according to known methods. For example, in each pixel, color may be represented by a mosaic of four sub-pixels, each sub-pixel corresponding to primaries such as red, green, or blue (where one primary is represented twice). The brightness of the overall pixel may be recorded by a one byte (i.e., 0-255) brightness value. According to one embodiment, images may be stored sequentially in data processor storage unit 19. The stored data may include one or more pixel properties, including color and brightness.

While, preferably, information gathering, storage and processing are performed by certain units, the system and method of the present invention may be practiced with alternate configurations. For example, the components gathering image information need not be contained in a capsule, but may be contained in any other vehicle suitable for traversing a lumen in a human body, such as an endoscope, stent, catheter, needle, etc.

Data processor storage unit 19 may store a series of images recorded by a capsule 40. The images the capsule 40 records as it moves through a patient's GI tract may be combined consecutively to form a moving image stream or movie.

According to an embodiment of the invention, the data processor 14 may include an editing filter 22 for editing a moving image stream. Editing filter 22 may be an editing filter processor and may be implemented by data processor 14. While the editing filter is shown in FIG. 1 as being separate from and connected to processor 14, in some embodiments editing filter may be a set of code or instructions executed by, for example, processor 14. Editing filter 22 may be or include one or more dedicated processors. The editing filter 22 may generate a subset of the original input set of images (the remaining images may be removed, or hidden from view). The editing filter 22 may evaluate the degree or occurrence in each frame of each of a plurality of pre-defined criteria from logical database 20. The editing filter 22 may select only a subset of images according to the predefined criteria, constraints, and rules provided by the logical database 20, to form a subset of images of interest. Preferably, the editing filter 22 may select for display only a portion of some images, for example a portion of an image which matches a predefined criteria, e.g. the portion of the image which received a high score according to the one or more rules or criteria provided in logical database 20. In selecting a portion, the portion may be made to fit a frame, and thus the portion may include non-selected image data.

According to one embodiment, editing filter 22 may select images or portions of images from one or more image streams captured by one or more imagers 46. The image streams may be processed separately, for example, each stream may be processed as a separate stream and images may be independently selected from each stream captured by a single imager 46. In other embodiments, streams may be merged, for example images from two or more streams may be sorted chronologically according to the capture time of the images and merged into a single stream. Other sorting methods are possible, for example based on different image parameters such as similarity between images, or based on the score assigned to the image portions by the pathology or abnormality detectors. The merged stream may be processed as one stream (e.g., editing filter 22 may select images from the merged stream instead of separately from each stream).

There are many factors to consider for efficiently reviewing in vivo images, various of which may affect the editing used in different embodiments. In one embodiment, the set of displayed images includes as many images as possible, which may be relevant to generate a correct diagnosis of the patient's condition by a health professional. It may be less desirable to omit certain highly informative images from the set of displayed images, to ensure correct diagnosis. Pathologies or abnormalities in human tissue have a very wide range of manifestation, making them in some cases difficult to detect. Accordingly, the editing filter 22 may select frames or portions of frames based on a specific predetermined criterion, or on a combination of a plurality of pre-determined criteria.

The pre-determined criteria may include, for example, a measure or score of one or more pathology detections and/or anatomical landmark detections (e.g., polyp detector, blood detector, ulcer detector, anomaly detector, duodenum detector, detectors of splenic and/or hepatic flexures in the colon, etc., which are determined based on color, texture, structure or pattern recognition analysis of pixels in the frames), a measure or score of visibility or field of view in the frame of biological tissue which may be distorted or obscured by features such as shadows or residue, the estimated location or region of the capsule (e.g., a higher priority may be assigned to frames estimated to have been captured in a particular region of interest), the probability that capsule is in preferred region (e.g., the colon in a colon imaging procedure, or the small bowel in a small bowel imaging procedure), secondary (non-image) sensor information (e.g., pH, pressure, electrical induction of sensors to determine the proximity of the capsule to the walls of the intestinal passages), capsule motion or motility, capsule orientation, frame capture or transmission rate, or any combination or derivation thereof. In some embodiments, the criteria used may be converted to scores, numbers or ratings before being evaluated with other criteria, so that the various criteria may be compared against each other.

The editing filter 22 may compute and assign one or more measures, ratings or scores or numbers to each frame based on one or more pre-determined criteria.

In some embodiments, a single criterion may be used to select a subset of images for display containing only image portions pertaining to the selected criterion. For example, each image may be scanned for polyps by a polyp detector. The polyp detector may produce a score of the probability of a polyp existing in the image, and may also provide estimated boundaries of that polyp in the image. Based on the estimated boundaries, only the relevant portion of the image may be extracted into the subset of selected images for display (see FIG. 2 for example).

In some embodiments, several different subsets of image portions may be selected for display, each subset pertaining to a different criterion. For example, one subset of images may include all images or portions of images associated with a high score or probability of polyp existance, while another subset of images may present all image or portions thereof relevant to or associated with blood or redness detection in the images. In some embodiments, the same image may be a part of two or more subsets of different criteria. It may be beneficial for a health care professional to view a subset of images including all image portions pertaining to the same symptom or pathology, since such view may increase the chance of correct diagnosis, e.g. quickly finding the true positives (e.g. the actual polyps) suggested by the filter 22, and easily identifying the false positives (portions of images which were wrongly detected by the filter 22 as polyps). Such a view may increase the positive predictive value (or precision rate, which is the proportion of patients with positive test results who are correctly diagnosed) of the endoscopic medical procedure. While the results of the filter 22 do not change, the specific method of display may cause the physician or health care professional to see the pathologies more easily on one hand, and to quickly pass over images which are clearly not pathologies (the false positives) on the other hand, thus improving the detection of true positives, and reducing the overall diagnosis time invested in a single case.

A score, rating, or measure may be a simplified representation (e.g., a derived value or rating, such as an integer 0-100) of more complex characteristics of an image or a portion of an image (e.g., criteria, such as, color variation, appearance of certain textural or structural patterns, light intensity of the image or portions thereof, blood detection, etc.). A score may include any rating, rank, hierarchy, scale or relative values of features or criteria. Typically a score is a numerical value, for example, a number from 1 to 10, but need not be limited as such. For example, scores may include, for example, letter (A, B, C, . . . ), signs or symbols (+, −), computer bit values (0, 1), the results of one or more decisions or conditions (yes no), for example, indicated by the status of one or more computing flags. Scores may be discrete (non-continuous) values, for example, integers, a, b, c, etc., or may be continuous, for example, having any real value between 0 and 1 (subject to the precision of computer representation of numbers). Any interval between consecutive scores may be set (e.g., 0.1, 0.2, . . . , or 1, 2, . . . , etc.) and scores may or may not be normalized.

Scores for each frame or portion thereof may be stored with the frames in the same database (e.g., image database 10). The scores may be defined, e.g., in a header or summary frame information package, with the data in an initial image stream or with frames copied to a second edited image stream. Alternatively or additionally, the scores may be stored in a database separate from the images (e.g., logical database 20) with pointers pointing to the images. The scores in separate database may be stored with associated predefined criteria, constraints, and rules to form a subset of selected image portions.

By using a score, the quantity of data used to represent the complex characteristics of the image may be reduced and therefore the complexity and computational effort of image comparisons is likewise reduced. For example, the editing filter 22 may attempt to determine if a criterion or feature is more visible in a portion of image A than in a portion of image B and then if the criterion or feature is more visible in a portion of image B than in a portion of image C. Without scores, the content of image B may be evaluated twice, once for comparison with image A and then again for comparison with image C. In contrast, using scores, according to embodiments of the invention, the content of each image need only be evaluated once with respect to each criterion to determine the score of the image. Once a score is assigned to image B or a portion thereof, a simple numerical comparison of scores (e.g., greater than, less than or equal to) may be executed to compare the image frame with both images A and C. Using a score to compare and select images may greatly reduce at least the number of times the content of an image is evaluated and thus the computational effort of image comparisons.

In one embodiment, the editing filter 22 may assign a single combined score, e.g., a scalar value, rating each frame or group of frames based on combined frame properties associated with two or more of the plurality of pre-determined criteria. The scores may be, for example, a normal or weighted average of frame values for each of the two or more pre-determined criteria. In one example, each frame may have a score, s1,s2,s3, . . . , assigned for each pre-determined criteria, 1, 2, 3, . . . , and the combined frame score, S, may be an average of scores, S=(s1+s2+s3)/c, where c is a scaling factor, or a weighted average, S=(w1*s1+w2*s2+w3*s3)/c, where w1, w2, and w3, are respective weights for each pre-defined criteria. In another example, the combined frame score, S, may be a product of scores, S=(s1*s2*s3)/c or S=(s1*s2+s2*s3+s1*s3)/c.

In another embodiment, the editing filter 22 may store each score individually for each individual criterion. For example, each frame may have a "score vector," S=(s1,s2, s3, . . . ), where each coordinate of the score vector provides a value for a different pre-defined criteria for the frame so that each criteria may be separately used, evaluated, and analyzed. By separating scores for each criterion, the editing filter may quickly compare scores for different combinations of criteria, for example, using vector operations. For example, when a subset of criteria (e.g., criteria 2 and 5) are selected to produce the subset of images for display, the editing filter 22 may quickly retrieve the corresponding scores (e.g., the second and fifth coordinates of the score vector S=(s2,s5)). A score vector may refer to any representation or storage that separates individual scores for each criterion, for example, such as a table or data array. In a score vector, the scores may be all in the same units (e.g., a number), but need not be.

The editing filter 22 may assign frames weighted scores, in which larger weights may be assigned for some pre-defined criteria than others. For example, since a large polyp (e.g., at least 6 mm in diameter) is more significant for diagnosis than a small polyp (e.g., 1 mm in diameter), the weight assigned to the large polyp score may be greater than the weight assigned to the small polyp score. While in some embodiments polyps are discussed, other pathologies, and other features, may be detected, rated, or scored. The score for each criterion may be weighted or combined in any suitable manner. In one embodiment, the weight of one score may affect the weight(s) of one or more other scores. For example, when one score exceeds a predetermined threshold, the weights of other scores may be changed in the combined score or the score may be added (e.g., the weight being changed from zero to one or more) or removed (e.g., the weight being changed from one to zero) from the combined score. In another embodiment, different weights for one or more scores may be used for different respective regions of the GI tract. For example, when a capsule is in (or is estimated to be) the colon (e.g., indicated by the location score or probability of being in the colon), a score indicating the tissue visibility may be given less weight because the relatively wide passage of the colon rarely obscures tissue visibility, thereby making the score less of a defining feature than other scores.

The scores or measures may be absolute or relative to each other. The absolute score(s) for each frame or portion of frame may be a value associated with the criteria for the single frame. The relative score(s) for each frame or for a portion of frame may be a change in the value associated with the criteria relative to the value associated with the criteria for a previous or adjacent frame. Both absolute and relative scores may or may not be scaled (normalized). Scores may be scaled with a different scaling factor, for example, for images captured or estimated to be captured within each region of the GI tract, each segment of the image stream or for each different frame capture and/or transmission rate.

The particular pre-determined criteria and their measures, ratings or scores used for selecting a subset of images for display in a two-dimensional tiled array layout may be preset (e.g., by a programmer or at a factory), automatically selected by the data processor 14 or the editing filter 22 itself and/or manually selected by a user (e.g., using input device 24). In, one embodiment, the editing filter 22 may always use one or more default criteria, for example, unless modified by a user. An editing graphical user interface (GUI) may enable a user to select from a plurality of possible criteria (e.g., 'select criteria' button of FIGS. 3A and B), from which a user may choose one or more. In another embodiment, the pre-determined criteria may be semi-automatically selected by a processor and/or semi--manually selected by a user. For example, the user may indirectly select pre-determined criteria by selecting the desired properties or constraints associated with the movie, such as a maximum movie length (e.g., 45 minutes or 9000 images), a review mode (e.g., preview movie, quick view mode, pathology detection mode, colon analysis mode, small bowel analysis mode, etc.), or other editing constraints. These parameters may in turn trigger the automatic selection of pre-determined criteria by a processor that meet the user-selected constraints.

The editing filter 22 may determine whether a frame or a portion of a frame corresponds to the selection criteria, and assign a score based on the level of correspondence. The editing filter 22 may compare the scores of each image portion to a predetermined threshold value or range. The editing filter may select for display each frame with a score exceeding (or lower than) the predetermined value or within the predetermined range for display. Accordingly, the editing filter 22 may not select for display (or may select for deletion) each frame with a score below the predetermined value or outside the predetermined range. In some embodiments, the score threshold may not be predetermined, but instead may be automatically calculated by editing filter 22 and/or data processor 14. The scores may be calculated, for example, based on the number of images in the original image stream (so that a predetermined number of input images satisfy the threshold or a predetermined percentage of input images satisfy the threshold), based on the number of images required in the selected set of images (so that a predetermined number of selected images satisfy the threshold), or based on a time limit for display of the selected set of images (so that the number of images that satisfy the threshold form a selected set of images with a viewing time of less than or equal to a predetermined time, for example when viewing the selected set of images in a standard or average display rate). In some embodiments a user may set these parameters, while in other embodiments the parameters may be predetermined or automatically generated by editing filter 22.

In some embodiments, the editing filter 22 may crop an image, to leave the relevant portion of the image (possibly within a frame such as a square or rectangle), and store it as a selected portion for display in the spatial layout. The original image or frame may be cropped based on the detected borders or edges of the pathology detector that caused the frame to be selected. For example, the original frame may be selected after receiving, for example, a high score by the polyp detector. The polyp detector may detect a polyp in a frame, and determine or estimate the polyp's edges. The editing filter may crop the original image and leave only the polyp (and some surrounding pixels) in the selected image portion, including the polyp's edges as determined by the detector. Similarly, frames which receive high scores based on other pathology detectors, may be cropped according to the determined edges or estimated borders of the detected pathology. In some cases, more than one pathology may be detected in a single frame, and multiple portions of the same frame may be selected for display in the spatial layout.

In some embodiments, the editing filter 22 may select images pertaining to certain anatomical landmark points in the body lumen traversed by the capsule 40, such as the entrance to the small bowel, duodenum, pylorus, terminal ileum, cecum, splenic flexure, or hepatic flexure. Other anatomical landmarks may be detected and selected for display by editing filter 22.

The editing filter 22 may include or may be embodied in one or more execution units for computing and comparing scores, such as, for example, an arithmetic logic unit (ALU) adapted executing arithmetic operation, such as add, multiple, divide, etc. The editing filter 22 may be or may be embodied in a processor (e.g., hardware) operating software. The editing filter 22 may include one or more logic gates and other hardware components to edit the original image stream to generate the edited image stream. Alternatively or additionally, the editing filter 22 may be implemented as a software file stored for example in logic database 20 or another memory, in which case a sequence of instructions being executed by for example data processor 14 results in the functionality described herein.

The original image stream may be divided into segments. A segment may be defined based on different parameters, such as a time parameter (e.g. a segment captured during one minute), a number of frames (e.g., 1000 consecutive frames), or frames associated with a detected or estimated anatomical region or landmark point in the body lumen (e.g., esophagus, stomach, small bowel, ascending colon, transverse colon, descending colon, cecum, duodenum, rectum, pylorus, etc.). In some embodiments, more than one parameter may be used concurrently to define a segment. For example, a colon segment of the original image stream may be represented by a number of images larger than a predetermined threshold in the subset of images. The colon segment may further be divided into sub-segments of, for example, a predetermined number of images (e.g., 100) or a predetermined time (e.g., 5 seconds). Each segment may be represented by at least a predetermined number of images or image portions (for example, one or two) selected for display in the spatial layout. The selected subset of images may be displayed in a rectangular tiled array layout on the screen or display 18.

A layout unit 28 may determine the arrangement of the image portions selected by editing filter 22 on the screen or display18. While the layout unit 28 is shown in FIG. 1 as being separate from and connected to processor 14, in some embodiments layout unit 28 may be a set of code or instructions executed by processor 14. Layout unit 28 may be or include one or more dedicated processors, Layout unit 28 may select or generate a spatial arrangement of a subset of the original image stream, including selected images or portions thereof. The spatial arrangement of the subset of image portions on the display 18 may be predetermined, or may be selected by a. user, for example from a list of possible layout arrangements using 'select arrangement' button of FIGS. 3A and B.

A user may prefer to view a layout which includes only the relevant portions of the selected frames, which comply with the predetermined or selected criteria or rules, for example portions of frames which receive a score which is higher or lower than a certain threshold determined for each type of selection criterion. For example, a rectangular tiled array made of 100 images may be generated for display, e.g. 10 rows and 10 columns of relevant portions of selected frames from the original input image stream. Preferably, all portions are arranged adjacent to each other, creating a tiled array with no white spaces or background spaces between the portions of frames, for example as shown in FIGS. 3A-3B, 4A-4C, and 5A-5B and 7. Such an arrangement may increase the visibility of pathological tissue if it exists in the displayed layout, since the tiled array may produce a homogenous view of the suspected image portions, and pathology may be prominent or may stand out in such distribution or arrangement. The selected image portions may be resized, for example by the layout unit 28, to an appropriate dimension or size, based on the selected layout, spatial arrangement and/or grid. In some embodiments the selected image portions may be resized to a single uniform dimension, while other embodiments allow for resizing or scaling the image portions displayed in the layout into different dimensions.

Relevant portions of the selected frames, as detected by the editing filter 22, may be arranged by layout unit 28 to maximize evenness or uniformity of the displayed array. The layout unit 28 may apply a filter (e.g., a "homogenizing" filter) to remove portions of frames which create an uneven, heterogeneous or noisy frame layout, or portions which have a disturbing effect on the eye of a user. For example, the layout unit 28 may minimize the occurrence of portions of images which may unnecessarily attract the physician's attention, such as dark portions of frames or portions with bad visibility due to intestinal juices or content, turbid media, bile, bubbles, image blurring, or other causes. Image portions which have been detected by editing filter 22 as complying with the selected criteria, may be subject to further processing or cropping, based on the detection of areas with bad visibility within the selected image portion. Such areas may be detected, for example, using methods known in the art, for example as disclosed in U.S. Pat. No. 7,577,283, which is assigned to the common assignee of the present invention and incorporated by reference in its entirety, and in particular, the method disclosed in FIG. 3 thereof. Portions of frames with bad visibility may be cropped from the displayed image portion, or the image portion may be removed completely from the displayed layout. Consequently, the occurrence of insignificant or irrelevant portions of images may be minimized in the displayed array of image portions, and the positive prediction and diagnosis value of the capsule procedure may increase.

The layout unit 28 may include or be embodied in one or more execution units for computing and comparing scores, such as, for example, an arithmetic logic unit (ALU) adapted executing arithmetic operation, such as add, multiple, divide, etc. The layout unit 28 may be a processor (e.g., hardware) operating software. The layout unit 28 may include one or more logic gates and other hardware components to edit the original image stream to generate the edited image stream. The layout unit 28 may be implemented as a software file stored for example in logic database 20 or another memory, in which case a sequence of instructions executed by for example data processor 14 result in the functionality described herein.

Once editing filter 22 selects the image portions, they may be merged by layout unit 28 to form a tiled array layout or grid. Different viewing arrangements or distributions of the image portions in the layout pages are described for example in FIGS. 4A, 4B and 4C. The resolution or number of image portions displayed in the layout may be predetermined, or may be selected by a user according to his/her preference, for example using select button 333 in FIGS. 3A and 3B. Different sizes of display layouts are described, for example, in FIGS. 5A and 5B.

Layout unit 28 may receive a set of selected image portions, and may determine which of the selected image portions will be displayed in each layout page. For example, the number of selected image portions from the original image stream may be 5,000. The generated or selected spatial arrangement of the layout pages may include 100 image portions in each layout page. Thus, 50 non-overlapping layout pages, each comprising different selected image portions, may be generated by the layout unit 28 and displayed to the user, for example sequentially (chronologically) or using a different sorting method such as a degree of similarity score between the selected portions. Typically, the physician may prefer keeping chronological order between the different layout pages, while the internal arrangement of the portions in a layout page may not be necessarily chronological. In another embodiment, the segmentation of image portions to specific layout pages may be determined based on the degree of similarity between images, or based on scores of different criteria which may be generated by the editing filter 22.

In one example, the layout pages may be displayed in a reverse chronological order, starting from the last image portions captured by the imager 46 and selected by editing filter 22, and finally showing the layouts including the image portions captured earlier chronologically. Such arrangement may be easier for a physician to view, since it may be similar to the direction typically viewed during a colonoscopy procedure (starting from the anus and eventually reaching the cecum area or further up the small bowel).

In one embodiment, the selected image portions may include duplicate copies of the frame portions selected from the original image stream, which may be stored separately from the original image stream in a second image stream. In another embodiment, the selected image portions may include a set of pointers or flags indicating which images and image portions of the original frames are selected for display, in the form of a rectangular array of image portions. A display application may display one or more rectangular arrays of the selected image portions, for example, by displaying those image portions indicated by flags or pointers, and may skip the unselected images or portions.

Reference is now made to FIGS. 2A and 2B. FIG. 2A shows an example of an image 200 which may be suspected as containing pathology, for example, a polyp detected by a polyp detector which may be included in editing filter 22. The polyp detector may indicate that edges 210 and 220 of image 200 are edges of suspected polyps. In one embodiment, only a relevant portion of the frame suspected as pathological may be selected for display in the grid or spatial layout. The size of each element (each image portion or each tile in the tiled array) in the spatial layout may be fixed and uniform for all elements, and may be selected by the user or predetermined by the system.

Preferably, each image portion is a rectangular, square or hexagonal portion of an image, which contains a suspected pathology, a suspected region of abnormality or a region which received a high score by at least one of the editing criteria selected in editing filter 22. The actual size in pixels of the portion selected for display may change, depending on the size of the suspected pathology detected in the image. In some embodiments, it may be beneficial to resize all suspected portions or selected images to a uniform size, thereby generating a homogenous display of suspected image portions or selected images. For example, the relevant regions indicated by edges 210, 220 suspected as pathological in the image 200 may be extracted from the image frame, for example by editing filter 22, processor 14 and/or layout unit 28. For example, image portions 211, 212 may be extracted from frame 200, and may then be cropped and resized by layout unit 28 (or another processor), to the determined uniform size for display in the final layout. In this method, the size of different pathologies, which may appear in different sizes in the original images, may be resized and displayed to an approximately uniform size. Since the cropping of the image portion may be performed based on the detected edges of the abnormality or pathology, the resizing may be performed without consideration of the original pathology size in the image. In other embodiments, the image portions may be cropped to a uniform size and not resized, for example smaller polyps will be cropped using more surrounding pixels in the resulting image portion (e.g., pixels located outside the pathology boundaries in the original image). In some embodiments, the complete image frames may be resized and displayed as thumbnails in the selected layout. For example, such functionality may be available when the user clicks an input device such as a mouse, on the specific image portion that he wishes to mark. In yet other embodiments, the image portions may be cropped and resized to different sizes, based on a selected grid and arrangement of the layout pages.

FIG. 2B shows portion 230 after being resized, for example, by layout unit 28. Portion 230 corresponds to portion 211 in image 200, and contains the edges 210 of a suspected polyp. Portion 230 has been cropped from original image 200 into a square or rectangular shape in order to fit into a tiled layout of a predetermined size (e.g., 9 rows and 11 columns of image frame portions). Similarly, other editing criteria or methods (e.g. blood or redness detector, ulcer detector, etc.) may determine different shapes and sizes of suspected pathologies in an image, and the relevant regions of the image may be cropped, such that only the suspected pathological tissue segment (and possibly background image portions) of the image is included in a rectangular, square or hexagonal portion and displayed to the user.

Figure 3B:
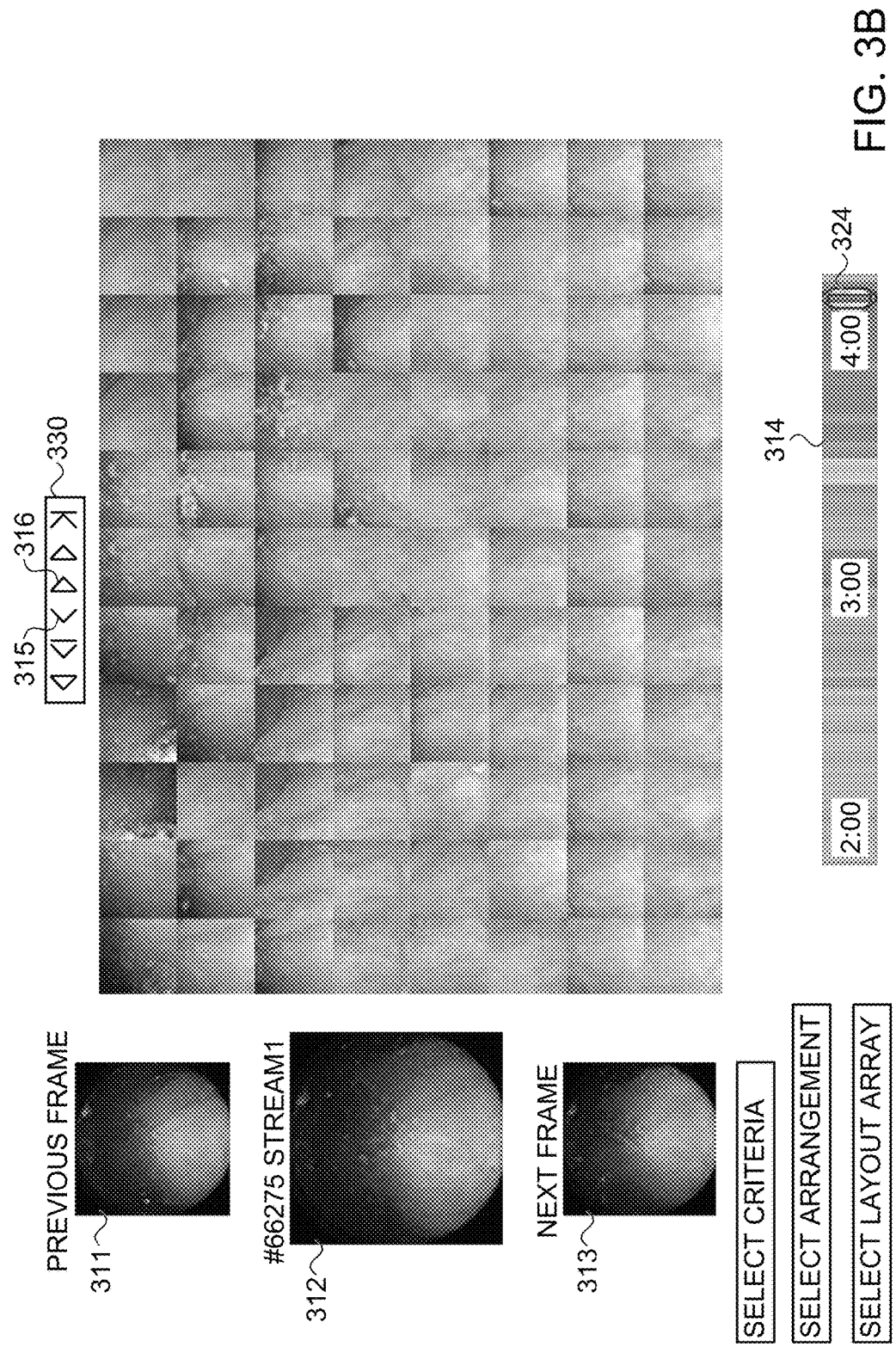

Reference is now made to FIGS. 3A and 3B, which are exemplary graphical user interfaces, showing an example layout containing pathological frame portions (3A) and another example layout containing normal tissue frame portions (false positives of the polyp detector) according to an embodiment of the present invention. All image portions shown in 3A and 3B are selected automatically by a processor (e.g. processor 14 or editing filter 22), for example based on polyp detection criteria. However, all portions of the layout shown in FIG. 3B include normal healthy tissue, and the physician reviewing the tiled layout may quickly conclude that it contains no pathologies, and go on to a next layout of image portions without spending extra time on the set of images of healthy tissue. Similarly, when reviewing the set of portions in FIG. 3A, a physician may conclude that portions included in segment 306 are also healthy tissue. On the other hand, most of portions of segment 310 in FIG. 3A are clearly pathological, containing a polyp, while the images in segment 308 may be more difficult to determine if pathological or not. The spatial layout including the image portions suspected as pathological may be easier for a physician to review and diagnose, than for example viewing a summary movie stream which may include only few sporadic occurrences of the pathological tissue, and which may be displayed using a fast frame rate.

Preferably, the user may control the time spent reviewing each layout, for example using (e.g. clicking on, using a pointing or other input device) "Previous" and "Next" buttons 315 and 316. When clicking on button 316, the next layout of image portions generated by the layout unit 28 of FIG. 1 may be displayed, while a previous layout may be displayed when clicking button 315. Other buttons 330 may be provided for the user, for example to jump to the last layout, jump to the first layout, or skip several layouts forward or backward. In one embodiment, the display may include a time/tissue bar 314, for example as described in U.S. Pat. No. 7,215,338, assigned to the common assignee of the present application. The bar 314 may include a cursor 324, which May indicate from which area or time of capture of the original image stream the current layout of image portions is taken. Such indication may be beneficial, for example, to assist the physician in assessing the area or anatomical region of the body lumen in which the pathology is located. The cursor 324 may change its size or width, for example in accordance with the layout of images which are currently displayed on the display device, in accordance with the number of images in the current layout; or in accordance with the number of images from which the displayed images (or portions) are selected. Windows 311, 312 and 313 may be displayed, for example, upon selection of one tile or image portion e.g. 325, and may show the complete image frame 312 from which the portion 325 was cropped, and the next and previous complete image frames 311 and 313, as they may appear in the original (input) image stream, in a selected subset of images or in a summary movie, In one example, the complete image frame 312 and the previous and next frames 311 and 313 may be automatically displayed to the user, for example upon movement of an input device (such as a mouse) over one of the image portions in the layout. A selection of an image portion or a double click with the mouse, for example, may open a segment of the image stream which includes the selected image portion (e.g., a few images before and a few images after the selected image or the image from which the portion was extracted). In some embodiments, marking an image portion in the layout page may automatically mark the image as a thumbnail in the original image stream. A workstation may receive a user indication of a selected image in the array (e.g., via a pointing device) and display the complete image frame corresponding to the selected image. In one embodiment, the user may select one or more frame portions 325, 326 and mark them for example as thumbnails, and may add comments, bookmarks or annotations. These selected thumbnails may be stored and presented to the user later, for example in an automatically generated report or while viewing the original movie stream or a summary movie stream.

The 'select criteria' button may include a list of selection criteria or rules, which a user may select for determining which image portions are selected for display in the layout pages. The 'select criteria button' may include high-level detection options, such as Polyp Detection, Lesion Detection, Inflammation Detection, Bleeding Detection, etc. in one embodiment, one or more rules/criteria may be selected by the user, while other embodiments allow criteria to be predetermined or preprogrammed in advance. The user may decide, for example, to choose only image portions indicated as suspected bleeding images, or may choose to view all images detected as suspected pathologies by at least one of the available detectors. The 'select arrangement' button enables the user to select the specific spatial arrangement of image portions in the layout. Several spatial arrangements of image portions are described in FIGS. 4A-4C hereinbelow. The 'select layout array' button enables the user to select the number and/or size of image portions that will appear in the rows and columns of the array.

In some embodiments, layout unit 28 may receive multiple streams of images, for example captured by one or more imagers 46 of capsule 40, e.g. imaging heads 57 and 58 of FIG. 1. The plurality of streams may be arranged in several different methods for display. For example, a simultaneous presentation of the separate image streams may be selected, displaying several image portions selected from each image stream in a single layout. In one embodiment, the left side of the layout may include the selected image portions from imaging head 57, while in the right side of the layout may be arranged selected image portions from imaging head 58. In another example, the layout division between the separate imaging heads may be dynamic, for example based on the amount of image portions selected in a certain time period from each imaging head 57 and 58. For example, during 10 minutes of the image capturing procedure 30 images may be selected from one imager and 70 images may be selected from another imager. In one embodiment, 100 image portions may be displayed simultaneously in a single layout screen, the 30 image portions from imaging head 57 may be positioned in the left columns of the layout, and the 70 image portions from imaging head 58 may be positioned in the remaining (right) columns of the layout page. A user may change the internal layout arrangement between the imaging heads, for example arrange the images from imaging head 57 on the top rows of the layout, and the images from imaging head 58 on the bottom part of the layout. In another embodiment, the layout may include image portions from a single imager only. A first layout page may display selected image portions captured by imaging head 57, while the next layout page may display selected image portions captured by imaging head 58. Other arrangements are possible.

The spatial arrangement of the set of layout pages generated from a single imaging procedure may be consistent, e.g., once a user selects the preferred layout arrangement for a first layout page, it will be stored and used for all the layout pages. The user's eye may become accustomed to the distribution of the image portions in the selected layout arrangement. Using the same layout arrangement may increase the productivity of the review process, since a user may grow used to the arrangement, and may identify pathology image portions more easily, and/or may detect anatomical landmark points more quickly.

Figure 4A:
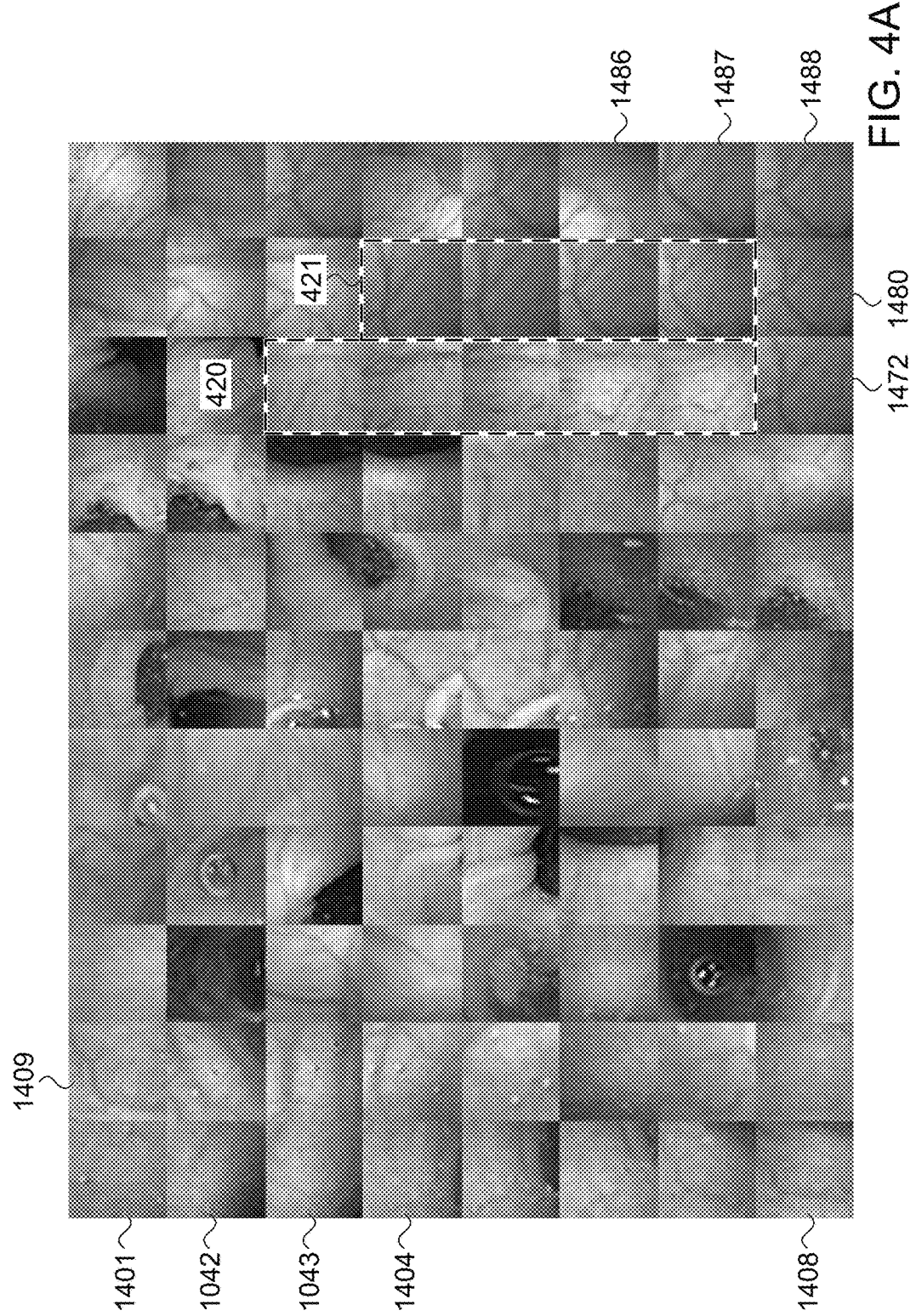
FIGS. 4A, 4B and 4C are exemplary display interfaces, showing different spatial arrangements of a layout of image portions according to an embodiment of the present invention.
Figure 4B:
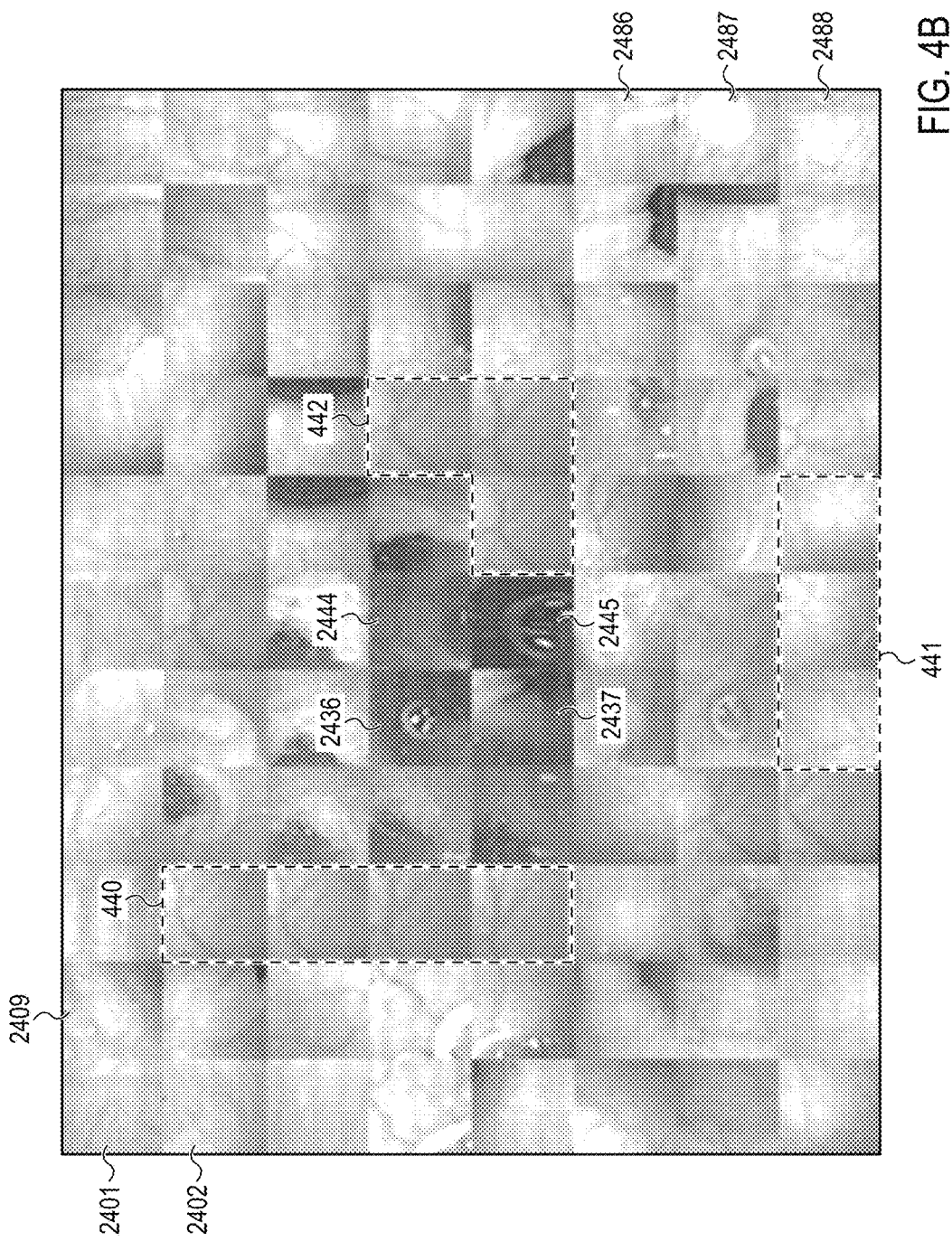
Figure 4C:
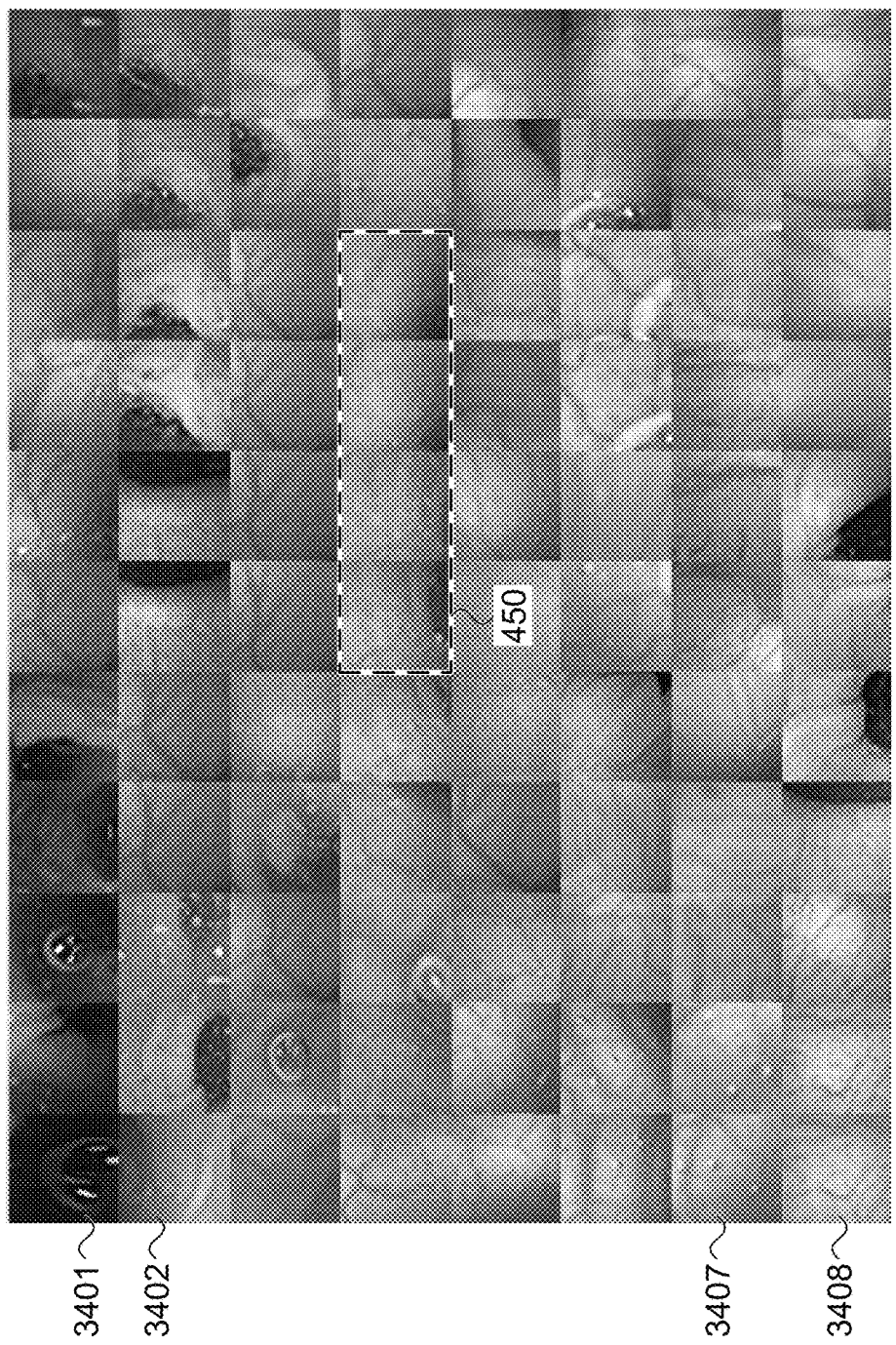

Reference is now made to FIGS. 4A, 4B and 4C, which are different spatial arrangements of display layouts according to embodiments of the present invention. Different parameters may be used for positioning the image portions on the screen. For example, the image portions may be sorted according to illumination intensity of the image (or portion), according to the chronological time of capturing the image, according to the degree of similarity between the image portions, according to color parameters (e.g. in the RGB portion, R pixels' median value of the portion) or based on other features, for example scores of criteria or features which were used for selection of the image portions from the original captured image stream. The different spatial layout arrangements may provide a better viewing experience for the user, and may reduce overall viewing time of the image portions layouts, and/or the image stream. Another parameter for positioning the frame portions may be the degree of similarity between chronologically sequential images, which may be preferably kept continuous or in the same area of the grid or array rather than separated in the layout. The images may be spatially ordered based on the scores, time, or other criteria.

FIG. 4A shows a first example of spatial arrangement of image portions in an array. The image portions are extracted from a subset of images, the subset of images selected from the original set of captured images, according to predetermined criteria. The image portions in this example are displayed in chronological order, arranged in an array in columns from left to right (in each column the images are chronologically arranged from top to bottom). The image portions are arranged in order according to increasing capture time, first by column (e.g., from top to bottom), then by row (e.g., from left to right or vice versa). Other orderings may be used, for example the image portions may be arranged according to decreasing capture time, and criteria other than time may be used (e.g., similarity, scores received by one or more detectors or criteria used in editing filter 22, etc.). The layout of image portions shown may represent, for example, a segment of the original image stream, which was captured during a certain time frame. For example, the image portions 1401-1488 may have been extracted from images captured during several minutes of the capsule's passage through the body lumen, e.g. images captured during the last 10 minutes of the original image stream. Portion 1401 was extracted from an image captured earlier in the original image stream than the images from which portions 1402-1488 were captured, portion 1402 was extracted from an image captured after the time of capture of 1401, etc. One advantage of arranging the selected portions according to their chronological order of capture is that similar image portions may be displayed next to each other, since sequences of several images captured while the capsule was in the same position are displayed in the sequential order of their capture timestamp. For example, the sequences 420 and 421 are examples of similar image portions which are kept together due to the chronological spatial arrangement.

In some embodiments, the number of selected image portions to be displayed to the user may be predetermined or selected by the user. The sensitivity of the criteria detectors, e.g. one or more thresholds determining whether an image portion is selected for display in the layout or not, may be adjusted accordingly, such that the required number of images will be selected for display based on the selection criteria. For example, the number of selected image portions may be a predetermined constant, e.g. 5,000 images or portions thereof, or may be a changing parameter, which may depend for example on the amount of images which pass one or more predetermined threshold values based on the selection criteria. If more images are selected, the sensitivity of the displayed layouts may increase, since more information is presented to the user, and the likelihood of a certain image of interest not being displayed decreases. On the other hand, when the number of image portions for display increases, the number of false positive images (e.g., images that depict or correspond to healthy tissue, but nevertheless pass the threshold of at least one pathology detection/selection criteria) may increase, and thus reduce the effectiveness of the spatial layout review.

FIG. 4B illustrates a different spatial arrangement of selected image portions in an array or layout, in which image portions 2436, 2437, 2444, 2445 show intestinal lumen areas. Intestinal lumen areas are image portions that depict or correspond to the dark lumen hole in an image, which may show an open lumen or partially or completely closed lumen. In the spatial arrangement shown in FIG. 4B, portions depicting intestinal lumen areas are displayed in the center of the layout, while image portions that contain tissue walls (e.g. 2401, 2402, 2409, 2486, 2487, 2488, etc.) are positioned around the periphery of the layout. Images that contain intestinal lumen portions may be detected, for example by the layout unit 28, using different techniques such as average image intensity, detection of a dark hole in the image, or other methods as known in the art. In one embodiment, the distance of the imaging device optical system from the imaged tissue may be estimated, for example using image intensity values. In another example, the degree of yellowness (e.g. the average or median intensity value of the blue plane of the RGB image, or the maximum value of a histogram generated based on the blue plane, or the average or median value of B/R) of the image may indicate that the tissue is distanced from the imaging device, for example due to bile which may be present between the optical system and the tissue. A more pinkish hue of the image may indicate that the imaging device is closer to the tissue wall. Any other distance assessment may be used, or any method of estimation of the distance of the capsule 40 from the imaged tissue. Layout unit 28 may determine the average or median value of, for example, blue pixels in the image portion, and estimate an approximate distance of the image portion from the imaging device based on such a value. Spatial arrangement of the lumen image portions in the center of the layout and tissue wall portions in the periphery of the layout may be similar to the structure of a typical single image captured by the capsule 40. Especially when travelling through the small bowel, or during forward movement of the capsule 40 in the colon, the capsule imaging system may typically be directed toward the center of the intestinal lumen area, and the captured image may contain portions of nearby tissue positioned in the periphery of the image and portions of open lumen approximately at the center of the image.

In some embodiments, sequences of similar images, for example sequences 440, 441, and/or 442, may be detected by layout unit 28 (or another processor), and may be kept in sequential position in the arranged layout, in order to keep the layout as uniform as possible, which may ease or simplify the process of identifying pathologies by the physician, since pathologies may stand out in the arranged layout. Keeping similar images or similar image portions jointly in a sequence or in the same neighborhood or area of the layout may assist a physician in distinguishing between healthy tissue and pathological tissue, since a plurality of continuous pathological tissue portions may stand out better than a single pathological tissue portion when scanning the layout. Similarly, when a reviewer is viewing a plurality of healthy tissue portions, the homogeneous arrangement may cause the healthy portions to seemingly blend in the layout with the other healthy tissue portions, and may be quickly scanned by the physician, thereby reducing the overall review time of the suspected image portion layouts.

Similarity between images or image portions may be implemented by using the EMD (Earth Mover's Distance) technique on color values of pixels of sequential frames, Euclidian difference (or normalized difference) between two images, or normalized cross correlation between images (and/or image portions). The images may be normalized, for example in gain and exposure time, prior to determination of similarity. When a plurality of image portions are determined as similar (e.g. passing a certain predetermined similarity threshold), the portions may be kept together in the layout, for example displayed adjacent to each other in sequential order in a row (e.g. sequence 440), column (e.g. sequence 441), or otherwise adjacent to each other (e.g. sequence 442). Once sequences are determined among the image portions to be displayed in the layout, the layout may be produced by arranging the different sequences spatially, according to a spatial arrangement selection. While the order between the sequences and their positioning in the layout may change, the order within each sequence may remain chronological.

FIG. 4C illustrates another embodiment of a spatial arrangement of the selected images or image portions in an array. In this array or layout, the portions depicting near tissue walls are positioned in the bottom rows of the layout (e.g., row of portion 3408, row of portion 3407), while the portions depicting the intestinal lumen hole or areas (or tissue which is farther from the capsule 40) are positioned in the top rows of the layout (e.g. row of portion 3401, row of portion 3402). When a user reviews the image portions using this arrangement, most of his attention may be directed at the top of the screen, since the top would typically include images that depict more information. Other spatial arrangements are possible, for example positioning the image portions in a snake-like manner. Similar portions may be kept in a sequence, e.g. sequence 450.

In some embodiments, the spatial arrangement of the image portions in the layout may be based on Space Filling Curves (also known as Peano curves), which are curves whose range may contain the entire 2-dimensional unit square. The image portions may be arranged along to a Peano curve which may be associated with the selected size of grid or array, for example a Hilbert curve. The image portions may be arranged along the Peano curve, for example chronologically, or may first be sorted based on similarity or other criteria (e.g. criteria in editing filter 22). For example, if the image portions are arranged based on similarity along the Peano curve, it may achieve better uniformity or evenness of the layout, since similar image portions may be arranged near each other, without large jumps or differences between one image portion and an adjacent or nearby image portion.

Figure 5A:
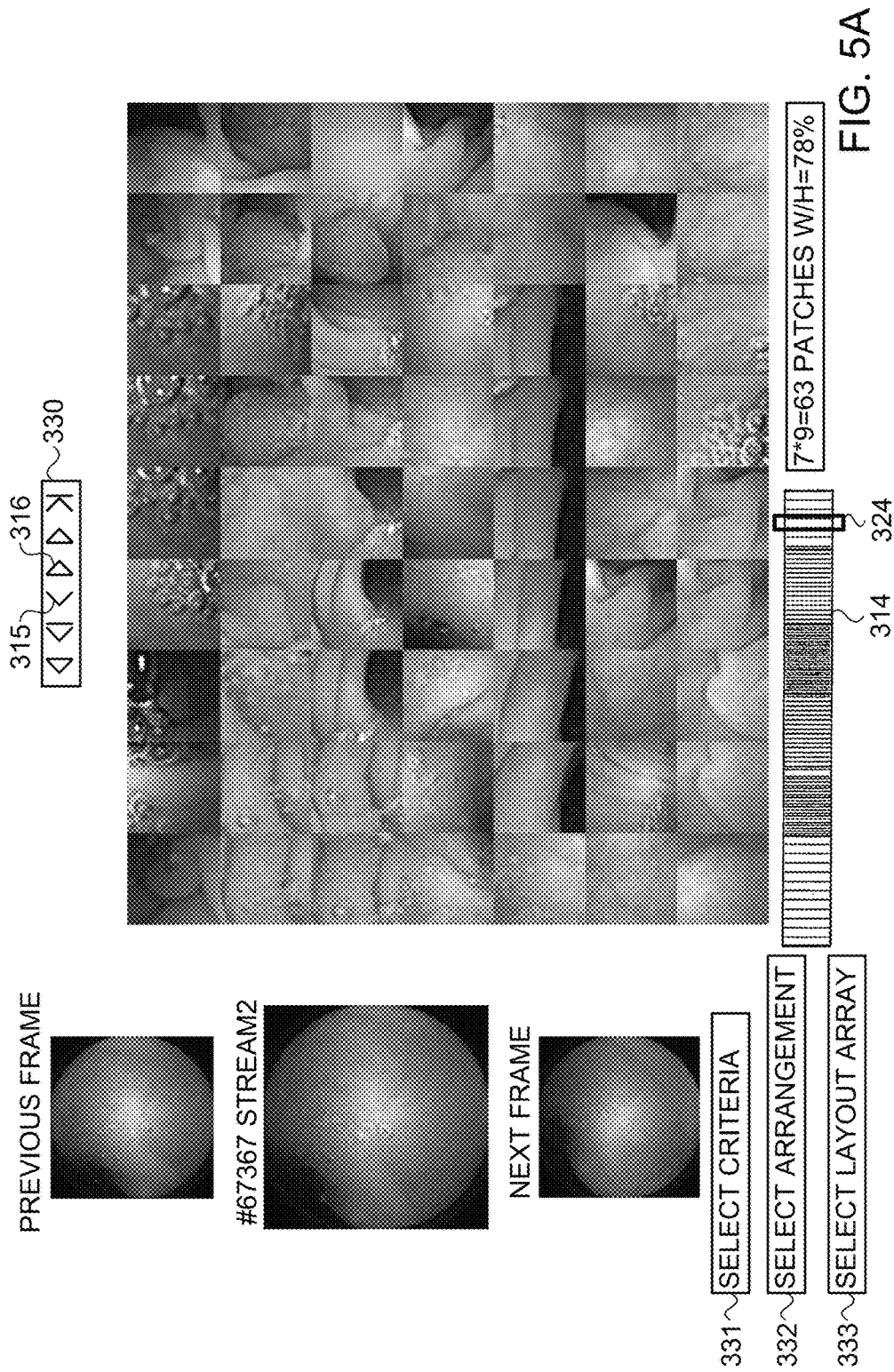

Reference is now made to FIGS. 5A and 5B, which depict different types of image portion arrays or layouts for display. In FIG. 5A, seven rows and nine columns of image portions are displayed, providing a height-to-width ratio (number of rows divided by number of columns) of 78%. In FIG. 5B, 10 rows and 12 columns are displayed, providing a height-to-width ratio of 83%. Other height-to-width ratios are possible, and in one embodiment a user may select and/or change the number of image portions displayed in a row or column according to his personal preference, for example using "select layout array" button 333. In one embodiment, a number of predetermined layout options may be provided to the user for selection through the user interface, while other embodiments may allow a user to freely select the number of rows and columns of image portions which will be displayed simultaneously in a single layout. Viewing more images on a single screen may reduce the viewing time of each layout, however, may make the review less effective. In another example, the selected array type may contain differently-sized windows for image portions. For example, the top rows may contain larger image portions, and the bottom rows may contain smaller image portions. When selecting or determining the array for display, the user may determine the number of image portions being displayed in a single array, the number of rows and columns being displayed, and/or the dimensions of each image portion.

Different parameters may affect the selected height-to-width ratio for display simultaneously on a single screen. For example, the user may want to quickly scan the layout on the screen and determine whether there is pathological tissue present or not in the current layout page. The height-to-width ratio may reflect a tradeoff between the viewing time required to scan all image portions, the size of the image portion which is displayed, and the amount of data which may be effectively scanned by a human eye without overlooking information. The optimal height-to-width ratio may change from one viewer to another.

Figure 6:
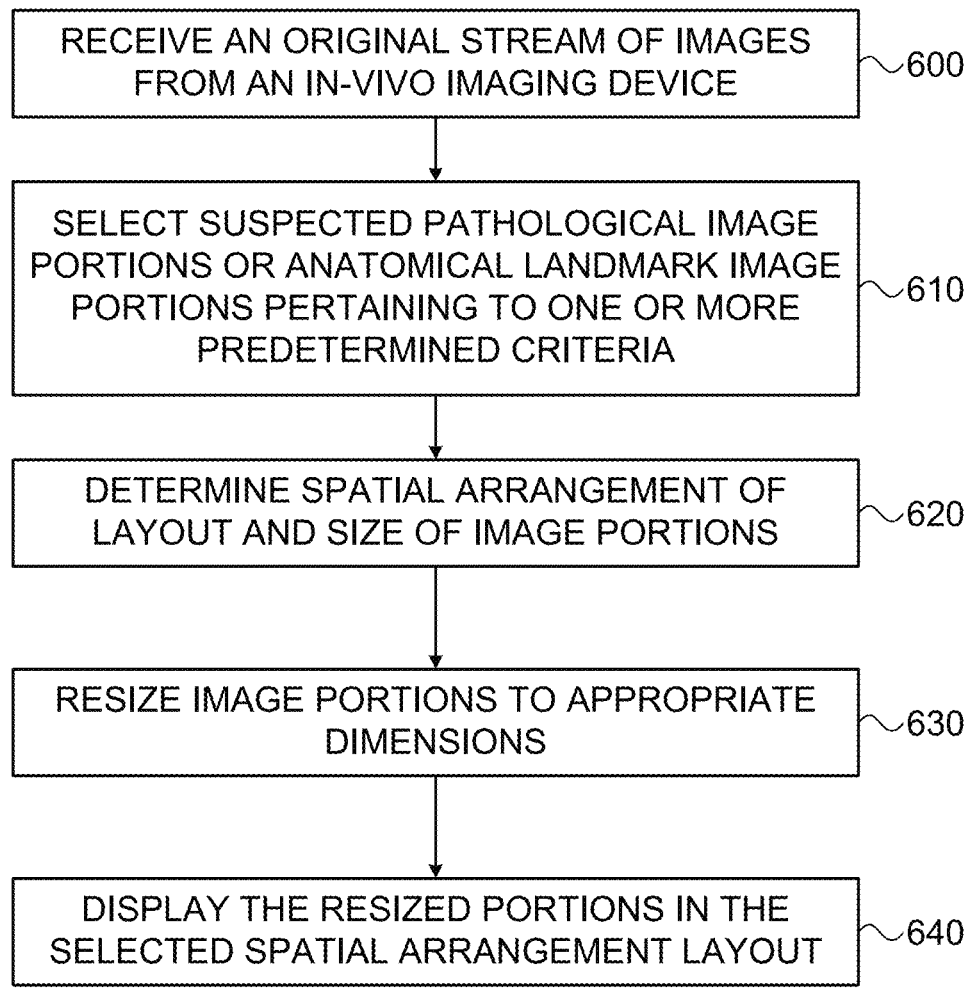
FIG. 6 is a flowchart of a method for displaying an array of image portions according to an embodiment of the present invention.

Reference is now made to FIG. 6, which is a flowchart of a method for displaying an arranged layout of images according to an embodiment of the present invention. In step 600, an original stream of images may be received from an in-vivo imaging device. The original stream of images may typically include every image captured by the imaging device during an in vivo imaging procedure, or may be pre-filtered or otherwise edited. The original image stream may be received by a wireless receiving device such as device 12 of FIG. 1, and/or may be received in a dedicated workstation or computer such as workstation 11 of FIG. 1.

In step 610, images or portions of images pertaining to or corresponding to one or more predetermined criteria (e.g., pathologies or anatomical landmarks) may be selected from the original stream of images. The criteria may be determined by a user, for example by selecting criteria from a list using the 'select criteria' button of FIGS. 3A and 3B, or may be predetermined, for example pre-programmed and stored in filter 22 or in data processor 14 of FIG. 1. In some embodiments, the selection of image portions according to the selection criteria may indicate that the image portion includes one or more suspected pathologies, such as bleeding, inflammation, polyps, lesions, celiac, tumors, Crohn's disease, etc. In another embodiment, the user may wish to determine exact anatomical landmark points of the image stream, and may select criteria pertaining to the anatomical landmark detection.

The number of selected image portions may be predetermined in some embodiments, or set by a user, or may be dependent on the amount of image portions that pass the (e.g., adjustable) threshold values of the selection criteria.

In step 620, the grid or array size (e.g, number of rows and number of columns of image portions) to be displayed in the spatial layout may be determined by a user. for example using the 'select layout array' button.In some embodiments, the grid size may be preselected, for example stored in the image layout unit 28. The spatial arrangement or distribution of the selected image portions along the layout page may be selected by a user (using the 'select arrangement' button) or preselected and stored in image layout unit 28.For example, the user may choose a uniformly-sized array of 8 rows and 11 columns of image portions in each layout page, and the internal distribution of the image portions in the layout may depend on the number of imaging heads capturing the images, and based on the preferred display of the user. Examples of different internal distributions of image portions in a layout include, but are not limited to, chronological order along columns and/or rows of the array, degree of similarity between selected ima.ge portions, distribution of image portions based on the estimated distance of the object in the image portion from the capsule's dome 54, etc.

The portions of the images may be resized in step 630 to the appropriate size or dimension, for example based on the selected grid arrangement and size, or based on other criteria, and according to the resolution properties of the screen display. In one embodiment, all image portions may be resized into uniform dimensions, then may be arranged in a matrix layout, e.g. a rectangular array of uniformly-sized image portions. In another embodiment, the selected array or layout for display may include differently-sized image portions, for example larger portions may be positioned in the middle of the layout, and smaller portions may be positioned around the periphery of the layout, or vice versa (smaller portions in the center and larger in the periphery of the array). Other layout distributions are possible.

In some embodiments, it is preferable to position the resized image portions with no spaces between them, such that image portions' edges are touching the adjacent portions' edges. In some embodiments, the edges of the image portions presented in the layout may be blurred and/or faded to reduce the visible borders between the image portions. The resized portions of images may be displayed in step 640, according to the selected spatial layout arrangement and grid size. Other steps may be included, and in some embodiments, not all steps may be performed.

Figure 7:
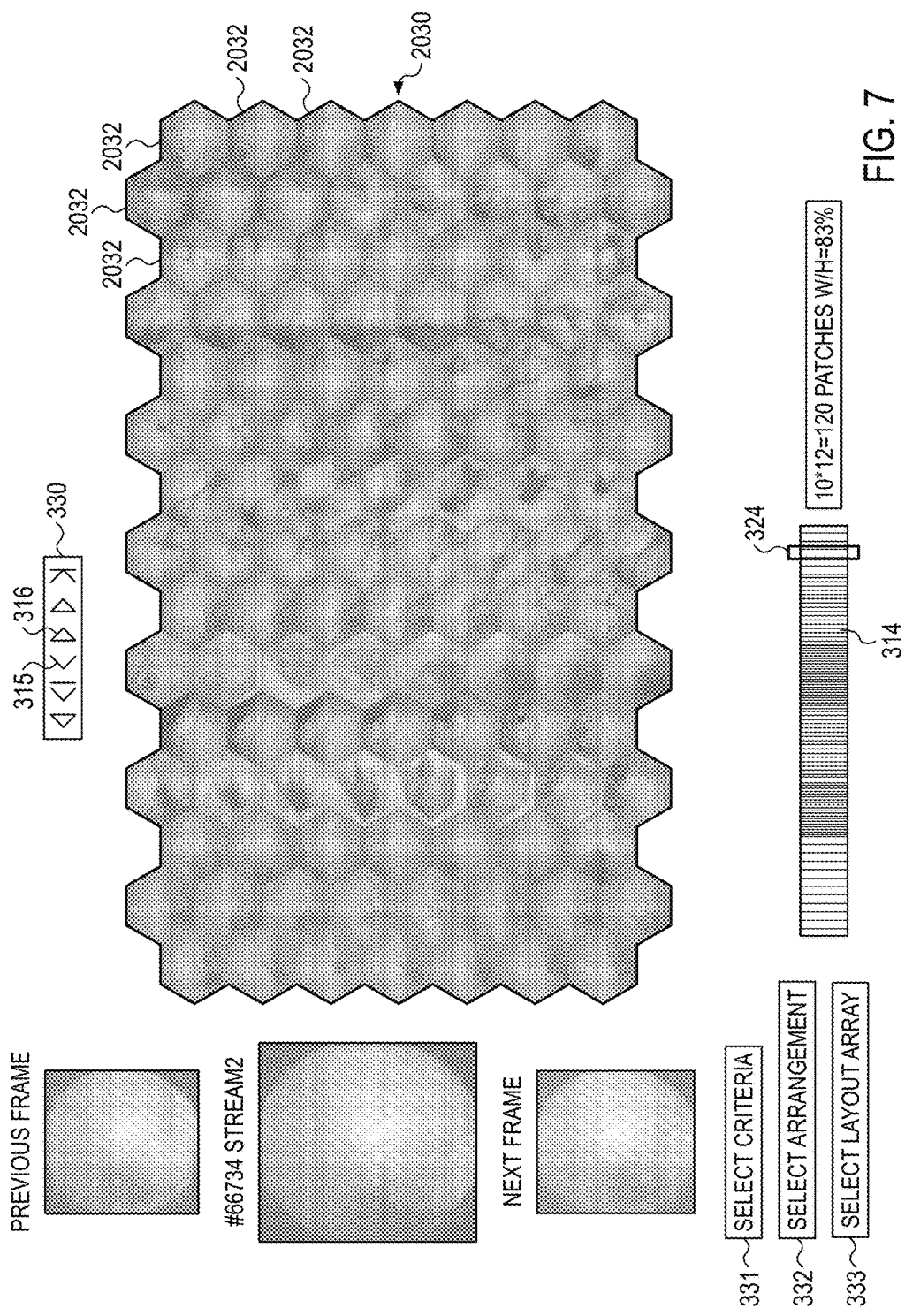
FIG. 7 is an example screen display according to an embodiment of the present invention.

Reference is now made to FIG. 7, an example screen display and graphical user interface (GUI) with a set of editing tools which may be displayed on a monitor, such as the monitor 18 of FIG. 1, according to an embodiment of the present invention.

In FIG. 7, image portions or in-vivo images are displayed to a user (e.g., on monitor 18) as one or more groups, collages or arrangements such as a group, array or grid 2030 of hexagons 2032, in this example touching one-another. The grid or group layout may include hexagonally bordered or shaped images.

While in the embodiments shown in FIG. 7 a certain number and arrangement of hexagons is shown, in other embodiments other arrangements and numbers may be used. The group 2030 may be displayed as an image stream. For example, a series of groups of hexagons may be displayed serially in the same position, as an image stream or movie is displayed, the difference being that multiple images are displayed in each time period, rather than one image per time period. Controls or buttons in FIG. 7 may be similar to those described with respect to FIGS. 3A and 3B.

In other embodiments the hexagons need not touch, or borders can be used. In one embodiment, one image frame or image, or portion thereof, is displayed per hexagon.

In one embodiment, images produced by the optical system of an imager such as device 40 are generally round. Display of an image or image portion which is round as a hexagon or in a hexagon-shaped window or portion, may allow less of an image to be removed or cut off when fitting to a hexagon shape than, for example, a square shaped display of the image. Hexagon shaped images may nest or fit together better than circular images, and hexagons can be tiled so that the area of the screen or display is used very efficiently. If the images are distorted to take up the full area of a window or shape, using a hexagon as such a shape may allow for less distortion than when using a square shape or image. In some embodiments, distortion to a square shape may result in distortion around the corners of the patch such that the edges between adjacent patches are more distinct and the viewing of the screen, and transitions from neighboring image to neighboring image, are less smooth. Such advantages may be more pronounced when some of the patches displayed are based on a whole or substantially whole frame.

In order to fit a round image to or within a hexagon, outer areas of the image can be cropped or cut off, or the round image can be warped or distorted (e.g., using distortion-minimizing mapping) into a hexagon shape. For example, the largest possible hexagon can be applied to the image, removing image pixels outside the hexagon. A combination of these techniques can be used. In a preferred embodiment warping or distortion is used instead of cropping so that no data is lost.

In one embodiment a typical image captured by an imaging device includes an interior round shaped portion which contains useful information, termed a valid mask, surrounded by a dark or otherwise not useful portion (extending from the inner round portion to the ir typically square border), The outermost portion, outside the valid mask, may be discarded. Reducing dark areas in the periphery in images may result in a smoother or more continuous collage or assembly of images, and smoother transitions between neighboring images (e.g., due to the lack or reduction of black borders due to dim lighting).

Outer portions of an image may be less useful for example due to the vignetting effect, a decrease in light or illumination towards the outer portion of the field of view.

In one embodiment, conformal mapping may be used to warp or conform the round image to the hexagonal frame. Conformal mapping may be computationally intensive, and thus in some embodiments a conformal mapping calculation may be performed once off-line, or before actual images are collected from a patient.

If offline computation is used, mapping may be done once, for example before images for a particular patient are gathered (and the mapping may be later applied to images actually gathered from a patient), or before the images are fully processed (and the mapping may be subsequently applied during processing). A mapping may be computed from a canonical circle to a canonical hexagon, or from a circle as defined from data received from a particular capsule. This transformation may be the conformal mapping. This initial computation may be done only once (if the valid mask is known or pre-determined, or deemed valid for all capsules), and the results saved to a file (in some resolution) or may be part of display software or a display system. This initial computation may be done once per capsule used, and the results applied to images for that particular capsule, as the input mask may vary from video to video or from capsule to capsule. The computation may be applied to every frame gathered from a patient.

Online computation may also be used in some embodiments.

Other user interface features may be used, and combinations of editing tools may be used.

Embodiments of the present invention may include apparatuses for performing the operations herein. Such apparatuses may be specially constructed for the desired purposes, or may comprise general purpose computers selectively activated or reconfigured by a computer program stored in the computers. Such computer programs may be stored in a computer readable storage medium, such as, but is not limited to, any type of disk including floppy disks, optical disks, CD-ROMs, magnetic-optical disks, read-only memories (ROMs), random access memories (RAMs) electrically programmable read-only memories (EPROMs), electrically erasable and programmable read only memories (EEPROMs), magnetic or optical cards, or any other type of media suitable for storing electronic instructions, and capable of being coupled to a computer system bus.

The processes and displays presented herein are not inherently related to any particular computer or other apparatus. Various general purpose systems may be used with programs in accordance with the teachings herein, or it may prove convenient to construct a more specialized apparatus to perform the desired method. It will be appreciated that a variety of programming languages may be used to implement the teachings of the invention as described herein.

The foregoing description of the embodiments of the invention has been presented for the purposes of illustration and description. It is not intended to be exhaustive or to limit the invention to the precise form disclosed. It should be appreciated by persons skilled in the art that many modifications, variations, substitutions, changes, and equivalents are possible in light of the above teaching. It is, therefore, to be understood that the appended claims are intended to cover all such modifications and changes as fall within the true spirit of the invention.

The invention claimed is:

1. A method for displaying portions of in vivo images, the method comprising:
    receiving a stream of in vivo images captured in a body lumen;
    automatically selecting images which correspond to suspected pathology from the stream;
    automatically cropping the selected images to remove portions of the selected image which do not comprise the suspected pathology and to obtain image portions of the selected images which comprise the suspected pathology;
        wherein the automatic cropping is performed such that the suspected pathology comprises a greater portion of each of the image portions of the selected images than the suspected pathology comprises in each of the selected images; and
    displaying the selected image portions arranged spatially in an array.

2. The method of claim 1, comprising determining a number of the image portions to be displayed in the array.

3. The method of claim 1, comprising:
    determining similarity between the selected image portions; and
    arranging similar image portions in a chronological sequence in the array.

4. The method of claim 1, wherein the selected image portions are displayed in the array adjacent to each other, with no spaces, background or borders between adjacent image portions.

5. The method of claim 1, wherein:
    the automatic selection is based on one or more selection criteria; and
    the one or more selection criteria are either predetermined or based on a user selection.

6. The method of claim 1 comprising selecting the array.

7. The method of claim 1, comprising automatically resizing the selected image portions based on a selected grid arrangement and size of the array.

8. The method of claim 1, wherein the automatic cropping is performed such that each of the image portions of the selected images comprises background pixels surrounding the suspected pathology in the image portions.

9. The method of claim 1, wherein the automatic cropping is performed based on detected edges of the suspected pathology in the selected images.

10. A system for displaying portions of in vivo images comprising:
    a processing unit to:
        receive a stream of in vivo images captured in a body lumen;
        automatically select images which correspond to suspected pathology from the stream; and
        automatically crop the selected images to remove portions of the selected image which do not comprise the suspected pathology and to obtain image portions of the selected images which comprise the suspected pathology, wherein the automatic cropping is performed such that the suspected pathology comprises a greater portion of each of the image portions of the selected images than the suspected pathology comprises in each of the selected images; and
    a display device to display the selected image portions arranged spatially in an array.

11. The system of claim 10 wherein the processing unit is configured to determine a number of the image portions to be displayed in the array.

12. The system of claim 10, wherein the processing unit is configured to:
    determine similarity between the selected image portions; and
    arrange similar image portions in a chronological sequence in the array.

13. The system of claim 10, wherein the selected image portions are displayed in the array adjacent to each other, with no spaces, background or borders between adjacent image portions.

14. The system of claim 10, wherein:
    the automatic selection is based on one or more selection criteria; and
    the processing unit is configured to determine one or more selection criteria for the automatic selection based on a user selection, or the one or more selection criteria are predetermined.

15. The system of claim 10 wherein the processing unit is to select the array.

16. The system of claim 10, wherein the processing unit is configured to automatically resize the selected image portions based on a selected grid arrangement and size of the array.

17. The system of claim 10, wherein the automatic cropping is performed such that each of the image portions of the selected images comprises background pixels surrounding the suspected pathology in the image portions.

18. The system of claim 10, wherein the automatic cropping is performed based on detected edges of the suspected pathology in the selected images.

* * * * *